United States Patent
Pierson et al.

(10) Patent No.: US 9,144,569 B2
(45) Date of Patent: Sep. 29, 2015

(54) METHODS OF ADMINISTERING AN AROMATASE INHIBITOR, PROSTAGLANDIN AND GNRH FOR REGULATING OVULATION IN CATTLE

(75) Inventors: Roger Pierson, Saskatoon (CA); Gregg Adams, Saskatoon (CA)

(73) Assignee: UNIVERSITY OF SASKATCHEWAN, Saskatoon, Saskatchewan (CA)

( * ) Notice: Subject to any disclaimer, the term of this patent is extended or adjusted under 35 U.S.C. 154(b) by 0 days.

(21) Appl. No.: 13/698,402

(22) PCT Filed: May 19, 2011

(86) PCT No.: PCT/CA2011/000578
§ 371 (c)(1),
(2), (4) Date: Jan. 16, 2013

(87) PCT Pub. No.: WO2011/143752
PCT Pub. Date: Nov. 24, 2011

(65) Prior Publication Data
US 2013/0116177 A1    May 9, 2013

Related U.S. Application Data

(60) Provisional application No. 61/346,662, filed on May 20, 2010.

(51) Int. Cl.
| | | |
|---|---|---|
| A61K 31/4196 | (2006.01) | |
| A61K 31/5575 | (2006.01) | |
| A61K 38/09 | (2006.01) | |
| A61D 19/00 | (2006.01) | |
| A61D 19/02 | (2006.01) | |
| A61K 38/24 | (2006.01) | |

(52) U.S. Cl.
CPC ......... *A61K 31/4196* (2013.01); *A61K 31/5575* (2013.01); *A61K 38/09* (2013.01); *A61K 38/24* (2013.01); *A61D 19/00* (2013.01); *A61D 19/02* (2013.01)

(58) Field of Classification Search
None
See application file for complete search history.

(56) References Cited

U.S. PATENT DOCUMENTS 5,227,375 A * 7/1993 Labrie et al. .................. 514/172

FOREIGN PATENT DOCUMENTS

| CA | 2444932 A1 | 10/2002 |
| CA | 2444980 A1 | 10/2002 |
| CA | 2472309 A1 | 10/2002 |

OTHER PUBLICATIONS

Baerwald et al., Biology of Reproduction, 2003; 69: 1023-1031.*
Johnson & Everitt, "Adult Ovarian Function" in Essential Reproduction, Johnson & Everitt, fifth edition (2000), by Blackwell Science Ltd Johnson & Everitt: pp. 85-86.*
Hong, Ann N Y Acad Sci. 2006; 1089: 237-51.*
Pursley et al., Theriogenlogy, 1995; 44: 915-923.*
Rettenmaier, Surg Gynecol Obstet. 1983; 156: 585-8: abstract only.*
Healey et al., Fertility Sterility, 2003; 80: 1325-1329.*
Hecker et al., Effects of Atrazine on CYP 19 Gene Expression and Aromatase Activity in Testes and on Plasma Sex Steroid Concentrations of Male African Clawed Frogs (*Xenopus laevis*). Toxicol Sci. Aug. 2005;86(2):273-280.
Ireland and Roche, Effect of progesterone on basal LH and episodic LH and FSH secretion in heifers. J Reprod Fertil. Mar. 1982;64(2):295-302.
Jee et al., Use of letrozole versus clomiphene citrate combined with gonadotropins in intrauterine insemination cycles: a pilot study. Fertil Steril. Jun. 2006;85(6):1774-1777.
Ji et al., Endogenous Opiates Regulate the Nocturnal Reduction in Luteinizing Hormone Pulse Frequency during the Luteal Phase of the Macaque Menstrual Cycle. Biol Reprod Dec. 1989;41(6):1024-1033.
Kastelic et al., Effect of day of prostaglandin F2[alpha] treatment on selection and development of the ovulatory follicle in heifers. Anim Reprod Sci. 1990;23(3):169-180.
Knopf et al., Ovarian Follicular Dynamics in Heifers: Test of Two-Wave Hypothesis by Ultrasonically Monitoring Individual Follicles. Domest Anim Endocrinol, Apr. 1989;6(2):111-119.
Lamb et al., Control of the estrous cycle to improve fertility for fixed-time artificial insemination in beef cattle: A review. J Anim Sci. Apr. 2010;88(13 Suppl.):E18I-E192.
Lane et al., Oestrous synchronisation in cattle—Current options following the EU regulations restricting use of oestrogenic compounds in food-producing animals: A review. Anim Reprod Sci. Dec. 2008;109(1-4): 1-16.
Malhi et al., Bovine Model for the Study of Reproductive Aging in Women: Follicular, Luteal, and Endocrine Characteristics. Biol Reprod. Jul. 2005;73(1):45-53.
Malhi et al., Bovine model of reproductive aging: Response to ovarian synchronization and superstimulation. Theriogenology Sep. 15, 2006;66(5):1257-1266.
Malhi et al., Oocyte developmental competence in a bovine model of reproductive aging. Reproduction Aug. 2007;134(2):233-239.
Mamali et al., The effect of albendazole administration on the concentration of ovarian steroids in the follicular fluid and the maturation of oocytes in the ewe. 16th International Conference of Animal Reproduction: Poster Abstracts. 2008;P501:192-193.
Mapletoft et al., The use of controlled internal drug release devices for the regulation of bovine reproduction. J Anim Sci, 2003;81(14 suppl 2): E28-36.
Martinez et al., Induction of Follicular Wave Emergence for Estrus Synchronization and Artificial Insemination in Heifers. Theriogenology, Sep. 15, 2000;54(5):757-769.
Mihm and Evans, Mechanisms for Dominant Follicle Selection in Monovulatory Species: A Comparison of Morphological, Endocrine and Intraovarian Events in Cows, Mares and Women. Reprod Dom Anim. Jul. 2008;43 Suppl. 2:48-56.
Miller et al., Interaction of estradiol and a nonsteroidal follicular fluid substance in the regulation of gonadotropin secretion in the mare. Biol Reprod. Mar. 1981;24(2):354-358.

(Continued)

*Primary Examiner* — Christina Borgeest
(74) *Attorney, Agent, or Firm* — Michael A. Whittaker; Acuity Law Group, P.C.

(57) ABSTRACT

Described herein are methods for synchronizing ovulation in a herd, inducing superovulation in a single animal, and improving frequency of successful implantation and development of fertilized ova.

19 Claims, 29 Drawing Sheets

(56) References Cited

OTHER PUBLICATIONS

Miller et al., Ovarian effects of bovine follicular fluid treatment in sheep and cattle. Biol Reprod. Oct. 1979;21(3):537-544.
Mitwally and Casper, Use of aromatase inhibitor for induction of ovulation in patients with an inadequate response to clomiphene citrate. Fertil Steril. Feb. 2001;75(2):305-309.
Mitwally and Casper, Aromatase inhibition for ovarian stimulation: future avenues for infertility management. Curr Opin Obstet Gynecol. Jun. 2002;14(3):255-263.
Mitwally and Casper, Aromatase inhibition improves ovarian response to follicle-stimulating hormone in poor responders. Fertil Steril. Apr. 2002;77(4):776-780.
Mitwally and Casper, Aromatase inhibition reduces the dose of gonadotropin required for controlled ovarian hyperstimulation. J Soc Gynecol Investig, Sep. 2004;11(6):406-415.
Mitwally and Casper, Potential of Aromatase Inhibitors for Ovulation and Superovulation Induction in Infertile Women. Drugs, 2006;66(17):2149-2160.
Mitwally and Casper, Single-dose administration of an aromatase inhibitor for ovarian stimulation. Fertil Steril. Jan. 2005;83(1):229-231.
Mitwally et al., Letrozole step-up protocol: A successful superovulation protocol. Fertil Steril. Apr. 2008;89(Suppl 2):S23-S24.
Nasser et al., Ovarian Superstimulatory Response Relative to Follicular Wave Emergence in Heifers. Theriogenology Oct. 1993;40(4):713-724.
Official Journal of the European Union, L 262, Oct. 14, 2003. Directive 2003/74/EC of the European Parliament and of the Council on Sep. 22, 2003 amending Council Directive 96/22/EC concerning the prohibition on the use in stockfarming of certain substances having a hormonal or thyristatic action and of beta-agonist. Brussels, Belgium, Sep. 22, 2003. Available at http://www.fve.org/veterinary/pdf/food/directive_2003_74.pdf :pp. 17-21.
Peter et al., Compilation of classical and contemporary terminology used to describe morphological aspects of ovarian dynamics in cattle. Theriogenology Jun. 2009;71(9):1343-1357.
Pierson and Ginther, Reliability of Diagnostic Ultrasonography for Identification and Measurement of Follicles and Detecting the Corpus Luteum in Heifers. Theriogenology, Dec. 1987;28(6):929-936.
Price and Webb, Steroid Control of Gonadotropin Secretion and Ovarian Function in Heifers. Endocrinology, May 1988;122(5):2222-2231.
Rawlings et al., The Influence of Estradiol-17beta and Progesterone on Peripheral Serum Concentrations of Luteinizing Hormone and Follicle Stimulating Hormone in the Ovariectomized Ewe. Theriogenology Nov. 1984;22(5):473-488.
Requena et al., Use of letrozole in assisted reproduction: a systematic review and meta-analysis. Hum Reprod Update Nov.-Dec. 2008;14(6):571-582.
Sanchez et al., Dosage of the Synthetic Progestin, Norgestomet, Influences Luteinizing Hormone Pulse Frequency and Endogenous Secretion of 17 beta-Estradiol in Heifers. Biol Reprod. Feb. 1995;52(2):464-469.
Savio et al., Effects of induction of low plasma progesterone concentrations with a progesterone-releasing intravaginal device on follicular turnover and fertility in cattle. J Reprod Fertil. May 1993;98(1):77-84.
Savio et al., Regulation of dominant follicle turnover during the oestrous cycle in cows. J Reprod Fertil, Jan. 1993;97(1):197-203.
Singh et al., Ultrasound image attributes of bovine ovarian follicles and endocrine and functional correlates. J Reprod Fertil Jan. 1998;112(1):19-29.
Sinha et al., Effect of CGS 20267 on ovarian aromatase and gonadotropin levels in the rat. Breast Cancer Res Treat. Mar. 1998;48(1):45-51.
Sioufi et al., Absolute Bioavailability of Letrozole in Healthy Postmenopausal Women. Biopharm Drug Dispos. Dec. 1997;18(9):779-789.
Sioufi et al., Comparative Bioavailability of Letrozole Under Fed and Fasting Conditions in 12 Healthy Subjects After a 2.5 Mg Single Oral Administration. Biopharm Drug Dispos. Aug. 1997;18(6):489-497.
Stock and Fortune, Ovarian Follicular Dominance in Cattle: Relationship between Prolonged Growth of the Ovulatory Follicle and Endocrine Parameters. Endocrinology Mar. 1993;132(3):1108-1114.
Taft et al., Exogenous Pulses of Luteinizing Hormone Cause Persistence of the Largest Bovine Ovarian Follicle. J Anim Sci. Dec. 1996;74(12):2985-2991.
Topipat et al., A comparison of the effects of clomiphene citrate and the aromatase inhibitor letrozole on superovulation in Asian women with normal ovulatory cycles. Gynecol Endocrinol. Mar. 2008; 24(3):145-150.
Umberger, Products Marketed to Promote Growth in Food-Producing Animals: Steroid and Hormone Products. Toxicology Jan. 1975;3(1):3-21.
US Food and Drug Administration, 2003. Compliance Policy Guides Manual, Sec. 608.400. Compounding of drugs for use in animals. Department of Health and Human Services. Available at http://www.fda.gov/ora/compliance_ref/cpg/cpgvet/cpg608-400compounding.pdf :pp. 1-7.
USDA Foreign Agricultural Service 2003. European Union Trade Policy Monitoring. Historic Overview and Chronology of EU's Hormone Ban. GAIN Report E23206. Available at http://www. http://www.fas.usda.gov/gainfiles/200311/145986773.pdf : 10 pp.
Valentini et al., An electrochemical ELISA procedure for the screening of 17-beta estradiol in urban waste waters. Analyst Oct. 2002;127(10):1333-1337.
Wilks and Hansel, Oxytocin and the Secretion of Luteinizing Hormone in Cattle. J Anim Sci Nov. 1971;33(5):1048-1052.
Yapura et al., Effects of a Single Dose of a Nonsteroidal Aromatase Inhibitor on Ovarian Function in Cattle. Reprod Fertil Dev. Jan. 2010;22(1):271.
Yapura et al,. Effects of a three-day regimen of letrozole on ovarian function in a bovine model. Vancouver, British Columbia, Canada, Sep. 29, 2010:1 page.
Yapura et al., Effect of a prolonged aromatase inhibitor treatment on pre-ovulatory ovarian follicles in cattle. Reprod Fertil Develop. Dec. 6, 2011;24(1):113.
Yapura et al., Effects of Vehicle and Route of Administration of Aromatase Inhibitor on Ovarian Function in Cattle. IETS 2011— Florida : 1 page.
Yapura et al., Effects of Vehicle and Route of Administration of Letrozole on Ovarian Function in Cattle, Reprod Fertil Develop. Jan. 2011;23(1):190.
Yapura et al., A bovine model for examining the effects of an aromatase inhibitor on ovarian function in women. Fertil Steril. Aug. 2011;96(2):434-438.e3.
Yapura et al., Effects of a non-steroidal aromatase inhibitor on ovarian function in cattle. Reprod Fertil Develop. 2012;24(4):631-640.
Zamberlam et al., Regulation of inducible nitric oxide synthase expression in bovine ovarian granulosa cells. Mol Cell Endocrinol. Mar. 30, 2011;335(2):189-194.
Adams et al., Effect of progesterone on ovarian follicles, emergence of follicular waves and circulating follicle-stimulating hormone in heifers. J Reprod Fertil. Nov. 1992; 96(2):627-640.
Adams et al., Effect of the dominant follicle on regression of its subordinates in heifers. Canadian Journal of Animal Science 1993;73:267-275.
Adams et al., Selection of a dominant follicle and suppression of follicular growth in heifers. Anim Reprod Sci, 1993;30(4):259-271.
Adams, Control of Ovarian Follicular Wave Dynamics in Cattle: Implications for Synchronization & Super Stimulation. Theriogenology, 1994;41(1):19-24.
Adams and Pierson, Bovine Model for Study of Ovarian Follicular Dynamics in Humans. Theriogenology 1995;43:113-120.
Adams, Comparative Patterns of Follicle Development and Selection in Ruminants. J Reprod Fertil Suppl. Aug. 1998;54:17-32.
Al-Fadhli et al., A randomized trial of superovulation with two different doses of letrozole. Fertil Steril, Jan. 2006;85(1):161-164.

(56) References Cited

OTHER PUBLICATIONS

Amer, New Trends for Estrus Synchronization Using a Combination of Gonadotropins, Prostaglandin and Estradiol Cypionate in Dairy Cows. Internet J Vet Med. Nov. 9, 2007;3(2):1.

Andersson and Skakkebaek, Exposure to exogenous estrogens in food: possible impact on human development and health. Eur J Endocrinol. Jun. 1999;140(6):477-485.

AT-Taras et al., Reducing estrogen synthesis does not affect gonadotropin secretion in the developing boar. Biol Reprod. Jan. 2006;74(1):58-66.

Baerwald et al., A new model for ovarian follicular development during the human menstrual cycle. Fertil Steril. Jul. 2003;80(1):116-122.

Baerwald et al., Characterization of ovarian follicular wave dynamics in women. Biol Reprod. Sep. 2003;69(3):1023-1031.

Baracaldo et al., Superovulatory Response Following Transvaginal Follicle Ablation in Cattle. Theriogenology Apr. 1, 2000;53(6):1239-1250.

Bayar et al., Letrozole vs. clomiphene citrate in patients with ovulatory infertility. Fertil Steril. Apr. 2006;85(4):1045-1048.

Belanger et al., Determination of Nonconjugated and Conjugated Steroid Levels in Plasma and Prostate after Separation on C-18 Columns. Ann NY Acad Sci. 1990;595:251-259.

Benoit et al., Effect of a Nonsteroidal Aromatase Inhibitor on in Vitro and in Vivo Secretion of Estradiol and on the Estrous Cycle in Ewes. Domest Anim Endocrinol. Oct. 1992;9(4):313-327 (abstract only).

Bergfelt et al., Ovarian Synchronization Following Ultrasound-Guided Transvaginal Follicle Ablation in Heifers. Theriogenology Nov. 1, 1994;42(6):895-907.

Bergfelt et al., Ovulation synchronization following commercial application of ultrasound-guided follicle ablation during the estrous cycle in mares. Theriogenology Nov. 2007;68(8):1183-1191.

Bergfelt et al., Surges of FSH During the Follicular and Early Luteal Phases of the Estrous Cycle in Heifers. Theriogenology Oct. 1, 1997;48(5):757-768.

Bhatnagar, The discovery and mechanism of action of letrozole. Breast Cancer Res Treat 2007;105:7-17.

Bleach et al., Plasma inhibin A in heifers: Relationship with follicle dynamics, gonadotropins, and steroids during the estrous cycle and after treatment with bovine follicular fluid. Biol Reprod. Mar. 2001;64(3):743-752.

Bo et al., Exogenous Control of Follicular Wave Emergence in Cattle. Theriogenology, 1995;43(1):31-40.

Bo et al., Local versus systemic effects of exogenous estradiol-17 beta on ovarian follicular dynamics in heifers with progestogen implants. Anim Reprod Sci, 2000; 59(3-4):141-157.

Bo et al., Ovarian follicular wave emergence after treatment with progestogen and estradiol in cattle. Anim Reprod Sci, 1995;39(3):193-204.

Bodensteiner et al., Alterations in Follicular Estradiol and Gonadotropin Receptors During Development of Bovine Antral Follicles. Theriogenology Jan. 15, 1996;45(2):499-512.

Bridges et al., Follicular Growth, Estrus and Pregnancy After Fixed-Time Insemination in Beef Cows Treated with Intravaginal Progesterone Inserts and Estradiol Benzoate. Theriogenology, 1999;52(4):573-583.

Casper, Letrozole: ovulation or superovulation? Fertil Steril. Dec. 2003;80(6):1335-1337.

Cohen et al., Approval summary: Letrozole in the treatment of postmenopausal women with advanced breast cancer. Clin Cancer Res., Mar. 2002;8(3):665-669.

Colazo et al., Fertility following fixed-time AI in CIDR-treated beef heifers given GnRH or estradiol cypionate and fed diets supplemented with flax seed or sunflower seed. Theriogenology, Apr. 15, 2004;61(6):1115-1124.

International Preliminary Report on Patentability dated Nov. 20, 2012 as reported in PCT/CA2011/000578.

International Search Report and Written Opinion dated Aug. 22, 2011 as reported in PCT/CA2011/000578.

Cortinez et al., Hormonal profile and endometrial morphology in letrozole-controlled ovarian hyperstimulation in ovulatory infertile patients. Fertil Steril. Jan. 2005;83(1):110-115.

Davar et al., Comparison of the success rate of letrozole and clomiphene citrate in women undergoing intrauterine insemination. J Res Med Sci. Nov. 2006;11(6):382-387.

Daxenberger et al., Possible health impact of animal oestrogens in food. Hum Reprod Update May-Jun. 2001;7(3):340-355.

De Rensis et al., The Control of Follicular Dynamics by PGF2alpha, GnRH, hCG and Oestrus Synchronization in Cattle. Reprod Dom Anim. May 1999;34(2):49-59.

Evans et al., Endocrine and ovarian follicular changes leading up to the first ovulation in prepubertal heifers. J Reprod Fertil, Jan. 1994;100(1):187-194.

FEMA Drug Approval Package dated Jul. 25, 1997 part 1: pp. 1-276.

FEMA Drug Approval Package dated Jul. 25, 1997 part 2: pp. 276-551.

Fisher et al., A randomized double-blind comparison of the effects of clomiphene citrate and the aromatase inhibitor letrozole on ovulatory function in normal women. Fertil Steril. Aug. 2002;78(2):280-285.

Fritsche and Steinhart, Occurrence of hormonally active compounds in food: a review. Eur Food Res Technol. 1999;209(3):153-179.

Gibbs, Is Veterinary Compounding Illegal Under Federal Law? IJPC, 2004;8(6):449-451.

Ginther et al., Emergence and deviation of follicles during the development of follicular waves in cattle. Theriogenology Jul. 1, 1997;48(1):75-87.

Ginther et al., Temporal associations among ovarian events in cattle during oestrous cycles with two and three follicular waves. J Reprod Fertil. Sep. 1989;87(1):223-30.

Ginther et al., Follicle Selection in Cattle: Relationships among Growth Rate, Diameter Ranking, and Capacity for Dominance. Biol Reprod. Aug. 2001;65(2):345-350.

Ginther et al., Mechanism of follicle deviation in monovular farm species. Anim Reprod Sci. Oct. 15, 2003;78(3-4):239-257.

Ginther et al., Selection of the Dominant Follicle in Cattle: Role of Estradiol. Biol Reprod. Aug. 2000;63(2):383-389.

Gombe et al., Regulation of Blood Levels of LH in Bulls: Influence of Age, Breed, Sexual Stimulation and Temporal Fluctuations. J Reprod Fertil Dec. 1973;35(3):493-503.

Hafs et al., Control of the Estrous Cycle with Prostaglandin F2{Alpha} in Cattle and Horses. J Anim Sci, 1974;38(Suppl_I):10-21.

Health Canada. Drugs and Health Products. Veterinary Products. Questions and answer: Hormonal growth promoters. Accessed Jan. 25, 2009. Available at http://www.hc-sc.gc.ca/dhp-mps/vet/faq/growth_hormones_promoters_croissance_hormonaux_stimulateurs-eng.php.

Extended European Search Report issued in EP 11782809 dated Oct. 9, 2013.

Yapura et al., Effects of a Non-Steroidal Aromatase Inhibitor on Ovarian Function in Cattle. Graduate Studies Research Thesis Dept Veterinary Biomedical Sci, Univ Saskatchewan Jul. 2009:1-98.

Allaway et al. A single 20 mg dose of aromatase inhibitor (AI) does not affect folliculogenesis in the follicular phase of the menstrual cycle. In: 56th Annual Meeting of the Canadian Fertility and Andrology Society. Vancouver, British Columbia, Canada, 2010:41. Sep. 29, 2010.

Office Action issued in EP 11782809 dated Jun. 24, 2014.

Casper et al., Review: Aromatase Inhibitors for Ovulation Induction. J Clin Endocrinol Metab. Mar. 2006;91(3):760-771.

Notice of Opposition issued in corresponding New Zealand application dated Oct. 24, 2014.

\* cited by examiner

Figure 14

| Sample | Plasma E-17β concentration | | CV |
| --- | --- | --- | --- |
| | LC/MS | Elisa | |
| A | 164 | 160.2 | 1.7 |
| B | 66.4 | 58.5 | 9.0 |
| C | 3.0 | 3.4 | 7.9 |
| D | 10.9 | 12.9 | 11.9 |
| E | 330 | 296.6 | 7.5 |
| F | 4.9 | 3.4 | 26.9 |
| G | 4.34 | 6.0 | 22.9 |
| H | 4.5 | 3.4 | 20.4 |
| I | 10.2 | 11.4 | 7.7 |
| J | 5.08 | 5.3 | 3.0 |
| K | 6.2 | 5.4 | 9.4 |
| L | 11.8 | 11.3 | 3.1 |
| M | 17.3 | 18.3 | 3.6 |
| N | 15.1 | 15.1 | 0.2 |
| O | 8.7 | 7.0 | 15.3 |
| P | 12.5 | 12.0 | 2.9 |
| Q | 70.1 | 73.6 | 3.4 |
| R | 11.9 | 16.9 | 24.2 |
| | | Mean CV | 10.1 |

|  | Control | Letrozole | P-value |
|---|---|---|---|
| Treatment to ovulation | 5.1±0.26 | 6.1±0.25 | 0.006 |
| Max extant DF diamm (mm) | 12.4±0.53 | 14.6±0.51 | 0.007 |
| DF diamm at TX | 3.9±0.47 | 4.2±0.46 | 0.684 |

Figure 24

METHODS OF ADMINISTERING AN AROMATASE INHIBITOR, PROSTAGLANDIN AND GNRH FOR REGULATING OVULATION IN CATTLE

RELATED APPLICATIONS

The present invention is filed under 35 U.S.C. §371 as the U.S. national phase of International Application No. PCT/CA2011/00578, filed May 19, 2011, which designated the U.S. and claims priority to U.S. Application No. 61/346,662 filed May 20, 2010, the contents all of which are hereby incorporated by reference in their entirety.

FIELD OF THE INVENTION

The field of the invention generally relates to compounds, compositions and methods for synchronizing ovulation in a herd, inducing superovulation in a single animal, and improving frequency of successful implantation and development of fertilized ova.

BACKGROUND OF THE INVENTION

Reproduction in cattle can be inefficient, owing to a variety of factors including herd size and that cows in estrus are not always observed.

Previous artificial insemination (AI) protocols have been attempted, using multiple drug substances. Examples of previously attempted AI protocols are as follows:

| Name of Protocol | Number of interventions* including AI | Number of Drugs Used** |
|---|---|---|
| 7 day CO-Synch | 3 | 2 |
| 7 day CO-Synch + CIDR | 3 | 3 |
| 7 day OV-Synch + CIDR | 4 | 3 |
| 5 day OV-Synch + CIDR | 4 | 3 |
| MGA-Select | 4 | 3 |
| 7-11 Synch | 5 | 3 |

*Refers to the number of separate occasions on which the cows must be handled
In some protocols, more than one dose of a drug is administered.

However, AI programs remain inefficient. Such inefficiencies result in lower insemination frequencies, which reduces economic efficiencies. This is a significant problem in cattle reproduction.

Among the strategies used to control ovarian function in cattle, treatment with estrogen in combination with progesterone has been very effective for synchronizing follicle wave emergence and ovulation [1, 2]. Steroid-induced wave synchronization is brought about by regression of the dominant follicle followed by resurgence in circulating FSH and subsequent emergence of a new follicular wave at a consistent interval post-treatment. Steroid-induced regression of the dominant follicle is a result of a systemic alteration in feedback of estradiol and progesterone on pituitary release of LH and FSH [3]. Estradiol suppresses FSH release [4], and decreases LH pulse amplitude in sheep [5] and cattle [6]. Progesterone decreases LH pulse frequency and suppresses growth of the dominant follicle in a dose-dependent manner in cattle [7-12]. After metabolic clearance of exogenous estradiol, endogenous FSH surges therefore resulting in the emergence of a new wave of follicular development approximately 4 days after estradiol/progesterone treatment regardless of the stage of development of the dominant follicle at the time of treatment [1, 2, 13].

The use of natural or synthetic estrogens in food producing animals, however, has been the subject of considerable controversy (reviewed in [18]). Increasing concern regarding the toxicity of hormonal preparations used as growth promotants in cattle and the potential carcinogenic effects of steroid hormone residues in meat or milk [19-21] has led to a prohibition of the use of estradiol and other steroid hormones as growth promotants in animals designated for human consumption in all the member states of the European Union as of Jan. 1, 1989 [22]. Furthermore, the use of estradiol-17β and its ester derivatives for purposes of reproductive management was prohibited in the European Union on Oct. 14, 2006 [23]. These actions in Europe led to the subsequence prohibition of the use of estradiol esters in lactating dairy animals in New Zealand and Australia in 2007 [24]. Although the use of estradiol and zeranol (an estrogen-like compound) as growth promotants is still permitted in the United States [25] and Canada [26], they cannot be used for the purpose of estrus synchronization except by prescription and custom-compounding. However, veterinary compounding of pharmaceuticals for food-producing animals has recently come under scrutiny in the US and is discouraged [27, 28]. This situation negatively impacts the implementation of reproductive technologies in cattle production systems, limiting potential reproductive efficiency and genetic improvement provided by the use of artificial insemination and embryo transfer [24].

In this context, the development of alternative methods for controlling ovarian function in cattle is needed.

This background information is provided for the purpose of making known information believed by the applicant to be of possible relevance to the present invention. No admission is necessarily intended, nor should it be construed, that any of the preceding information constitutes prior art against the present invention.

SUMMARY OF THE INVENTION

In accordance with one aspect of the present invention there is provided methods for synchronizing ovulation in a herd, inducing superovulation in a single animal; and improved frequency of successful implantation and development of fertilized ova.

In one aspect of the present invention there is provided a method of synchronizing ovulation a mammal, comprising: administering an effective amount of an aromatoase inhibitor to said mammal so as to induce the formation of a persistent follicle and delay wave emergence by preventing spontaneous ovulation in said mammal; administering a luteolytic dose of a prostaglandin so as to induce regression of the corpus luteum of said mammal; administering an ovulatory does of GnRH or pLH to said mammal; and inseminating said mammal.

In another aspect of the present invention there is provided a method of synchronizing ovulation a mammal, comprising: administering an effective amount of a prostaglandin; administering an effective amount of an aromatase inhibitor; and inseminating said mammal.

In another aspect of the present invention there is provided a method of inducing superovulation in a mammal, comprising: administering an aromatase inhibitor to said mammal at the beginning of a follicular wave emergence in said mammal.

In another aspect of the present invention there is provided a method of improving fertility in a mammal, comprising: administering an aromatase inhibitor to said mammal in early esterus or mid-diestrus following insemination of said mammal.

In another aspect of the present invention there is provided a method of inducing double ovulation in a mammal, comprising: administering an aromatase inhibitor to said mammal from day 1 to day 7 following follicular wave emergence in said mammal.

In another aspect of the present invention there is provided a method of improving twinning in a mammal, comprising: administering an aromatase inhibitor to said mammal before dominant follicle selection; administering a luteolytic dose of a prostaglandin; and inseminating said mammal.

In accordance with another aspect of the present invention there is provided use of an aromatase inhibitor in a mammal so as to induce the formation of a persistent follicle and delay wave emergence by preventing spontaneous ovulation in said mammal; use of a luteolytic dose of a prostaglandin so as to induce regression of the corpus luteum of said mammal; and use for an ovulatory does of GnRH or pLH in said mammal for synchronizing ovulation in said mammal, wherein said mammal synchronized for ovulation is suitable for insemination.

In accordance with another aspect of the present invention, there is provided use of a prostaglandin; and use of an aromatase inhibitor for synchronizing ovulation in a mammal, wherein said mammal synchronized for ovulation is suitable for insemination.

In accordance with another aspect of the present invention, there is provided use of an aromatase inhibitor in a mammal at the beginning of a follicular wave emergence in said mammal for inducing superovulation in a mammal.

In accordance with another aspect of the present invention, there is provided use of an aromatase inhibitor in a mammal early esterus or mid-diestrus following insemination of said mammal for improving fertility in said mammal.

In accordance with another aspect of the present invention, there is provided use of an aromatase inhibitor in a mammal from day 1 to day 7 following follicular wave emergence in said mammal for inducing double ovulation in said mammal.

In accordance with another aspect of the present invention, there is provided use of an aromatase inhibitor in a mammal before dominant follicle selection; and use of a luteolytic dose of a prostaglandin for improving twinning in said mammal, wherein said mammal is suitable for inseminating.

In accordance with an aspect of the present invention, there is provided a kit for synchronizing ovulation in a mammal, comprising: an aromatase inhibitor so as to induce the formation of a persistent follicle and delay wave emergence by preventing spontaneous ovulation in said mammal; a luteolytic dose of a prostaglandin so as to induce regression of the corpus luteum of said mammal; an ovulatory does of GnRH or pLH; and instructions for the use thereof.

In accordance with an aspect of the present invention there is provided, a kit, comprising: a prostaglandin; an aromatase inhibitor; and instructions of the use thereof, for synchronizing ovulation in a mammal, wherein said mammal synchronized for ovulation is suitable for insemination.

In accordance with an aspect of the present invention there is provided, a kit, comprising: an aromatase inhibitor for use in a mammal at the beginning of a follicular wave emergence in said mammal for inducing superovulation in a mammal; and instructions for the use thereof.

In accordance with an aspect of the present invention there is provided, a kit, comprising: an aromatase inhibitor for use in a mammal early esterus or mid-diestrus following insemination of said mammal for improving fertility in said mammal; and instructions for the use thereof.

In accordance with an aspect of the present invention there is provided, a kit comprising: an aromatase inhibitor for use in a mammal from day 1 to day 7 following follicular wave emergence in said mammal for inducing double ovulation in said mammal; and instructions for the use thereof.

In accordance with an aspect of the present invention there is provided, a kit, comprising: an aromatase inhibitor for use in a mammal before dominant follicle selection; a luteolytic dose of a prostaglandin for improving twinning in said mammal; and instructions for the use thereof, wherein said mammal is suitable for inseminating.

BRIEF DESCRIPTION OF THE DRAWINGS

Embodiments of the present invention will now be described, by way of example only, with reference to the attached Figures, wherein:

FIG. 3($b$) is a line graph depicting plasma LH concentrations in heifers after a single intravenous dose of letrozole (plasma LH concentrations in heifers (percent change after treatment; mean±SEM) for 96 hours after a single intravenous dose of letrozole (high-, medium- and low-dose groups combined; n=29) given 4 days after follicular ablation (i.e., 2.5 days after wave emergence), compared to saline-treated controls (n=10));

Figure 7:
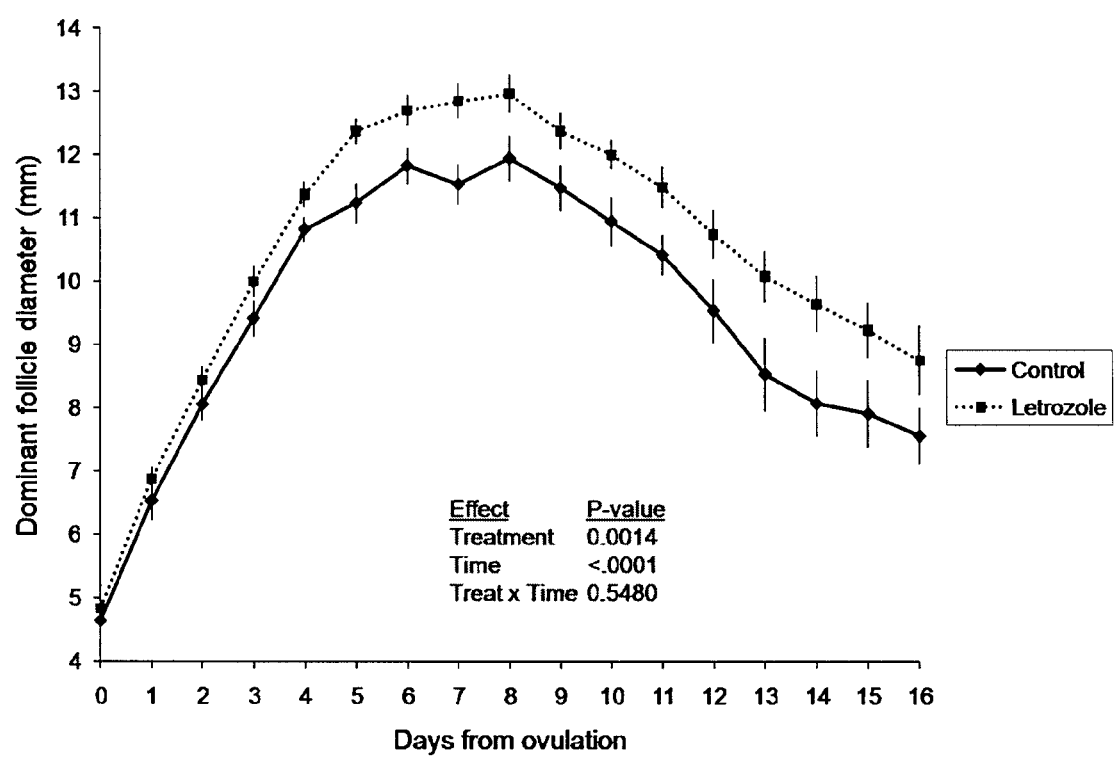
Figure 8:
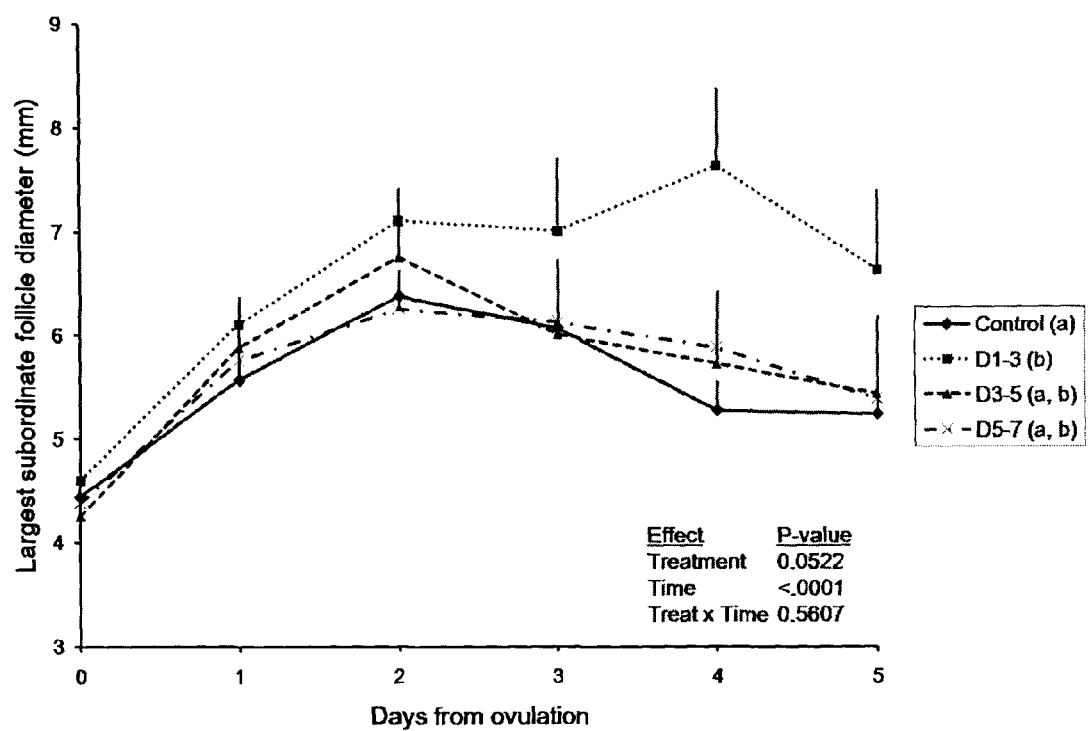
Figure 9:
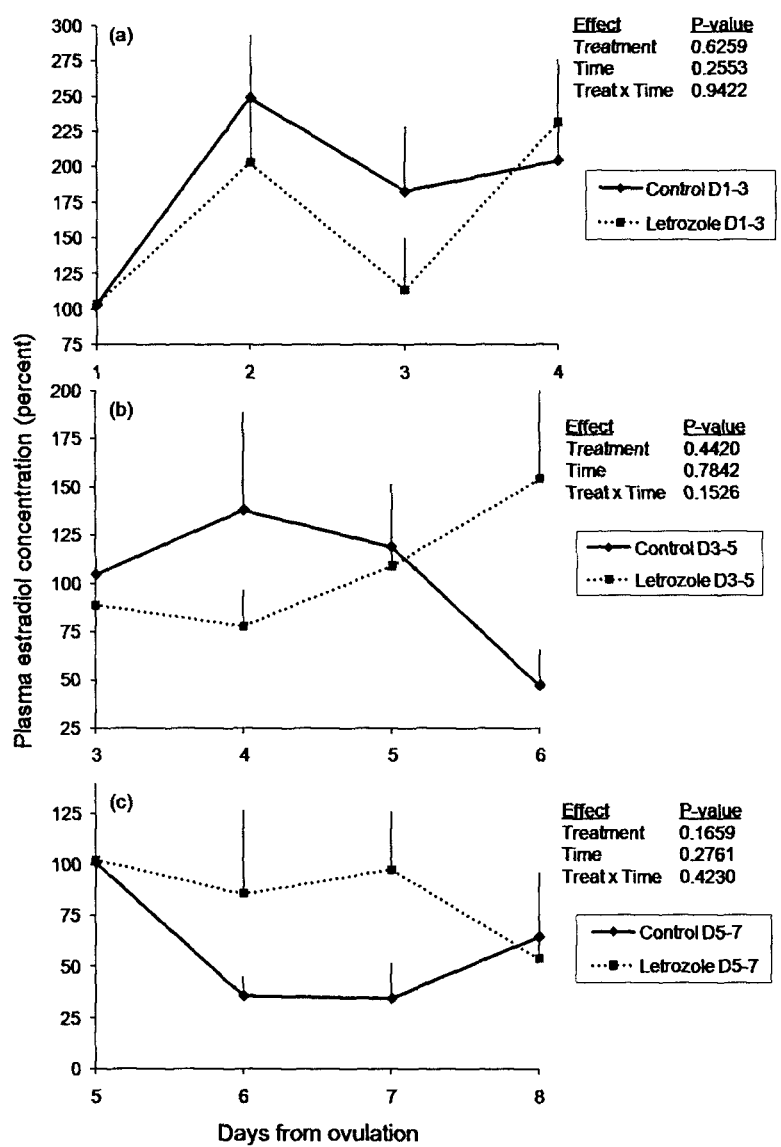
Figure 11:
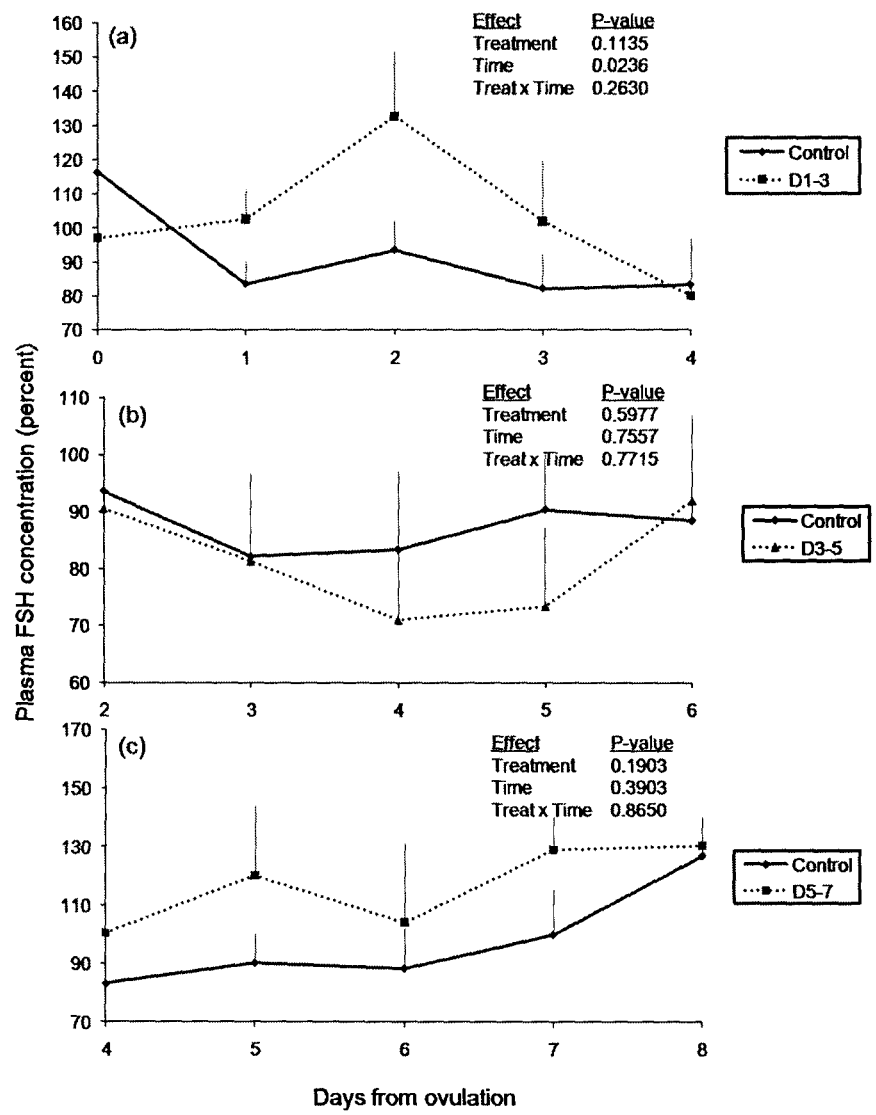
Figure 12:
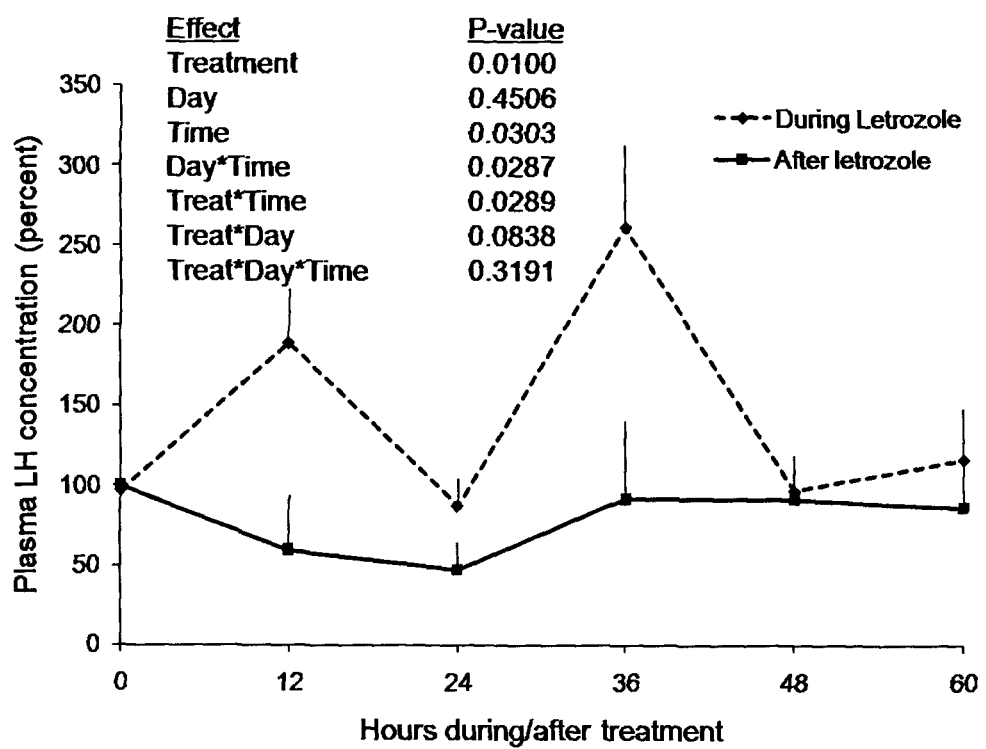
Figure 13:
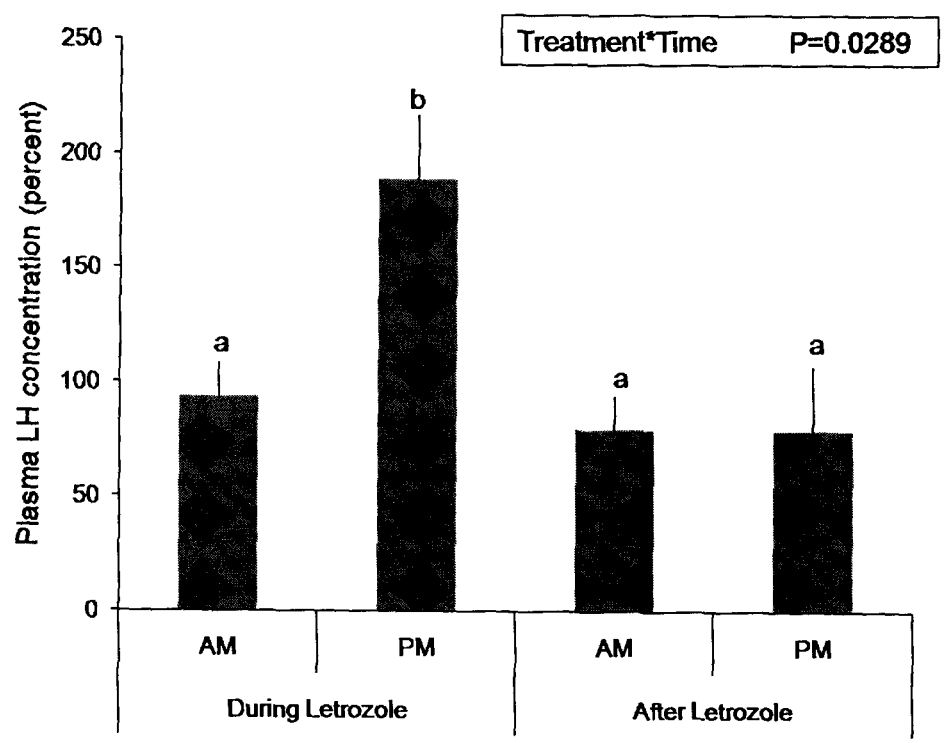
Figure 15:
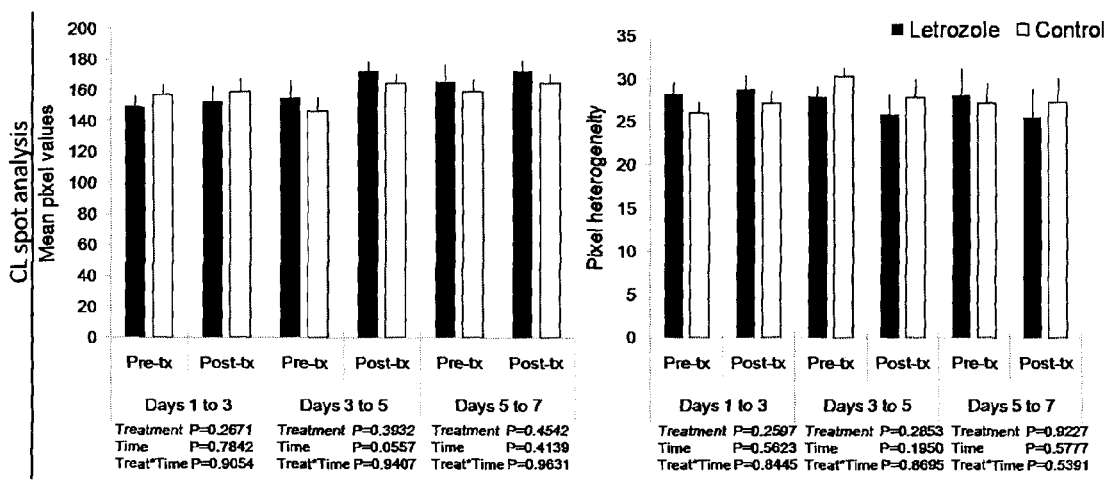
Figure 15:
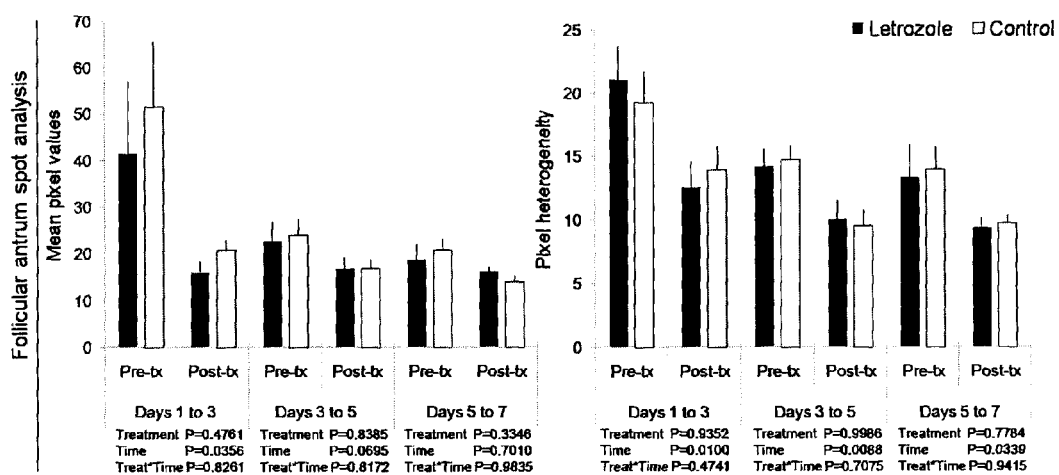
Figure 15:
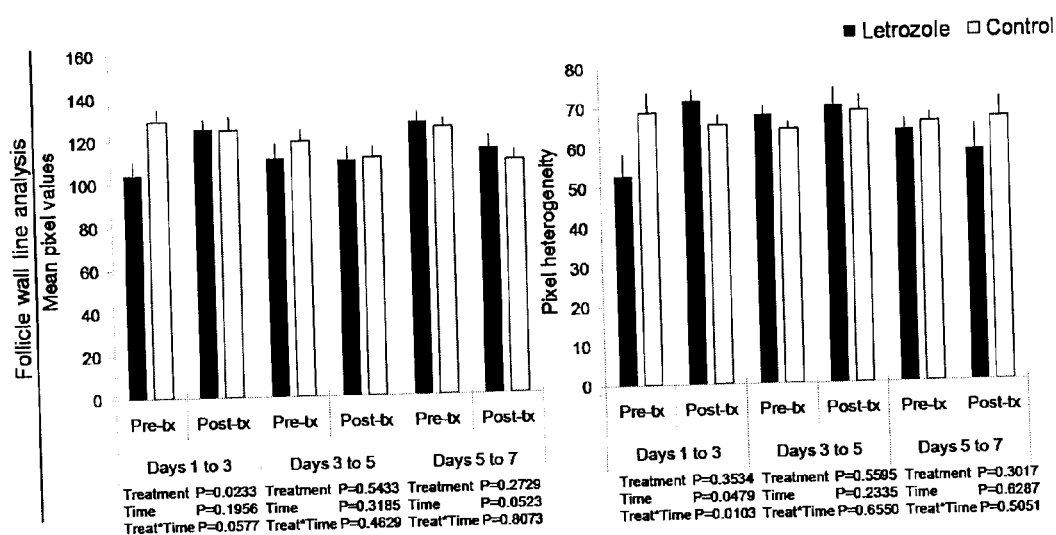

(Day 0=ovulation). $^{abc}$Overall means for treatment groups with no common superscript were different (P<0.05));

FIG. 7 is a line graph depicting a diameter profile of the dominant follicle in heifers treated with letrozole (diameter profile (mean±SEM) of the dominant follicle in heifers treated with letrozole on Days 1 to 3, 3 to 5 or 5 to 7 (Day 0=ovulation; treatment groups combined, n=28) compared to untreated controls (n=17));

FIG. 8 is a line graph depicting a diameter profile of the largest subordinate follicle in heifers treated with letrozole (diameter profile (mean±SEM) of the largest subordinate follicle in heifers treated with letrozole on Days 1 to 3 (n=10), Days 3 to 5 (n=9), or Days 5 to 7 (n=9; Day 0=ovulation), compared to untreated controls (n=17). $^{abc}$Overall means for treatment groups with no common superscript were different (P<0.05));

FIG. 9 is a line graph depicting plasma estradiol concentration (plasma estradiol concentration, expressed as a percent of the mean of two pre-treatment samples (i.e. taken 24 hours before and immediately before treatment; mean±SEM); in heifers following daily treatment with letrozole from Days 1 to 3 (a), Days 3 to 5 (b) and Days 5 to 7 (c) of the first follicular wave (n=5 per group; Day 0=ovulation));

FIG. 10(a) is a line graph depicting the diameter profile of the corpus luteum in heifers treated with letrozole (mean±SEM) in heifers treated with letrozole (85 μg/kg day for 3 days; data from treatment periods of Days 1 to 3, 3 to 5, and 5 to 7 combined; n=18), compared to untreated controls (n=17));

FIG. 10(b) is a line graph depicting the plasma progesterone concentration in heifers treated with letrozole (mean±SEM) in heifers treated with letrozole (85 μg/kg day for 3 days; data from treatment periods of Days 1 to 3, 3 to 5, and 5 to 7 combined; n=18), compared to untreated controls (n=17));

FIG. 11 is a line graph depicting plasma FSH concentration in heifers treated with letrozole (plasma FSH concentration, expressed as a percent of the mean of Days 0 and 1 (mean±SEM), in heifers treated with letrozole on Days 1 to 3 (n=10), Days 3 to 5 (n=9), or Days 5 to 7 (n=9; Day 0=ovulation), compared to untreated controls (n=17));

FIG. 12 is a line graph depicting a comparison of plasma LH concentration in heifers (comparison of plasma LH concentrations in heifers for a 60-hour period from the start of treatment and from the end of treatment with letrozole. Values (mean±SEM) are expressed as a percent of the mean of Days 0 and 1 in heifers treated with letrozole on Days 1 to 3 (n=10), Days 3 to 5 (n=9), or Days 5 to 7 (n=9; Day 0=ovulation). Data obtained during the 3 days of letrozole treatment and the 3 days after treatment were analyzed for effects of Treatment (during vs after), Time of data collection (AM vs PM), Day (1st, 2nd, and 3rd), and their interactions.);

FIG. 13 is a bar graph depicting the effect of letrozole on plasma LH concentrations (effect of letrozole on plasma LH concentrations (expressed as a percent of the mean of Days 0 and 1 post-ovulation; mean±SEM) in heifers treated in the morning for 3 consecutive days (letrozole-groups combined n=28) during the 3 days of treatment and after the 3 days following treatment. Remove box around stats.);

FIG. 14 depicts a table of estradiol concentrations;

FIG. 15 depicts bar graphs of CL spot analysis (mean pixel values (mean±SEM) and pixel heterogeneity (mean±SEM) of the CL recorded by spot analysis. Pre- and post-treatment values were compared within each treatment period (Days 1 to 3, Days 3 to 5 or Days 5 to 7) with contemporary controls.) [Panel A], follicular antrum spot analysis (mean pixel values (mean±SEM) and pixel heterogeneity (mean±SEM) of the follicular antrum recorded by spot analysis. Pre- and post-treatment values were compared within each treatment period (Days 1 to 3, Days 3 to 5 or Days 5 to 7) with contemporary controls) [Panel B] and follicle wall line analysis (mean pixel values (mean±SEM) and pixel heterogeneity (mean±SEM) along the follicular wall recorded by line analysis. Pre- and post-treatment values were compared within each treatment period (Days 1 to 3, Days 3 to 5 or Days 5 to 7) with contemporary controls.)[Panel C]

Figure 16:
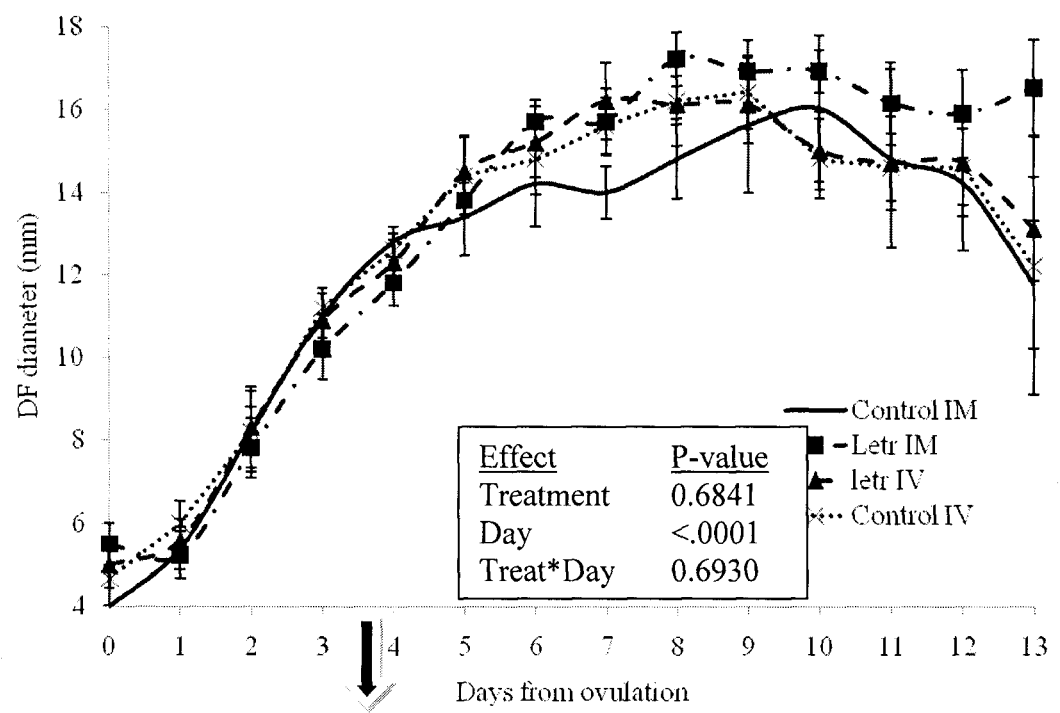
Figure 18:
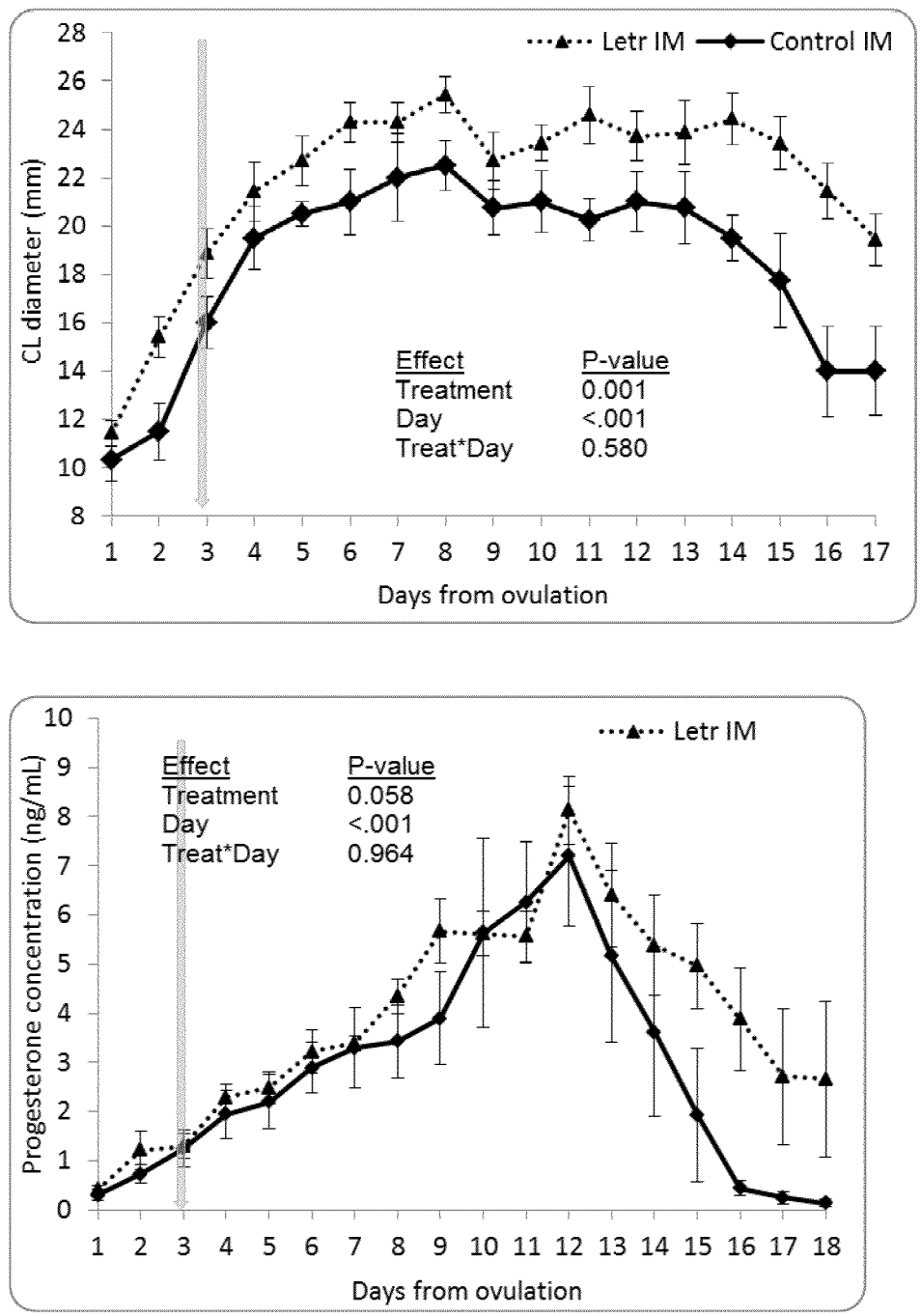
Figure 19:
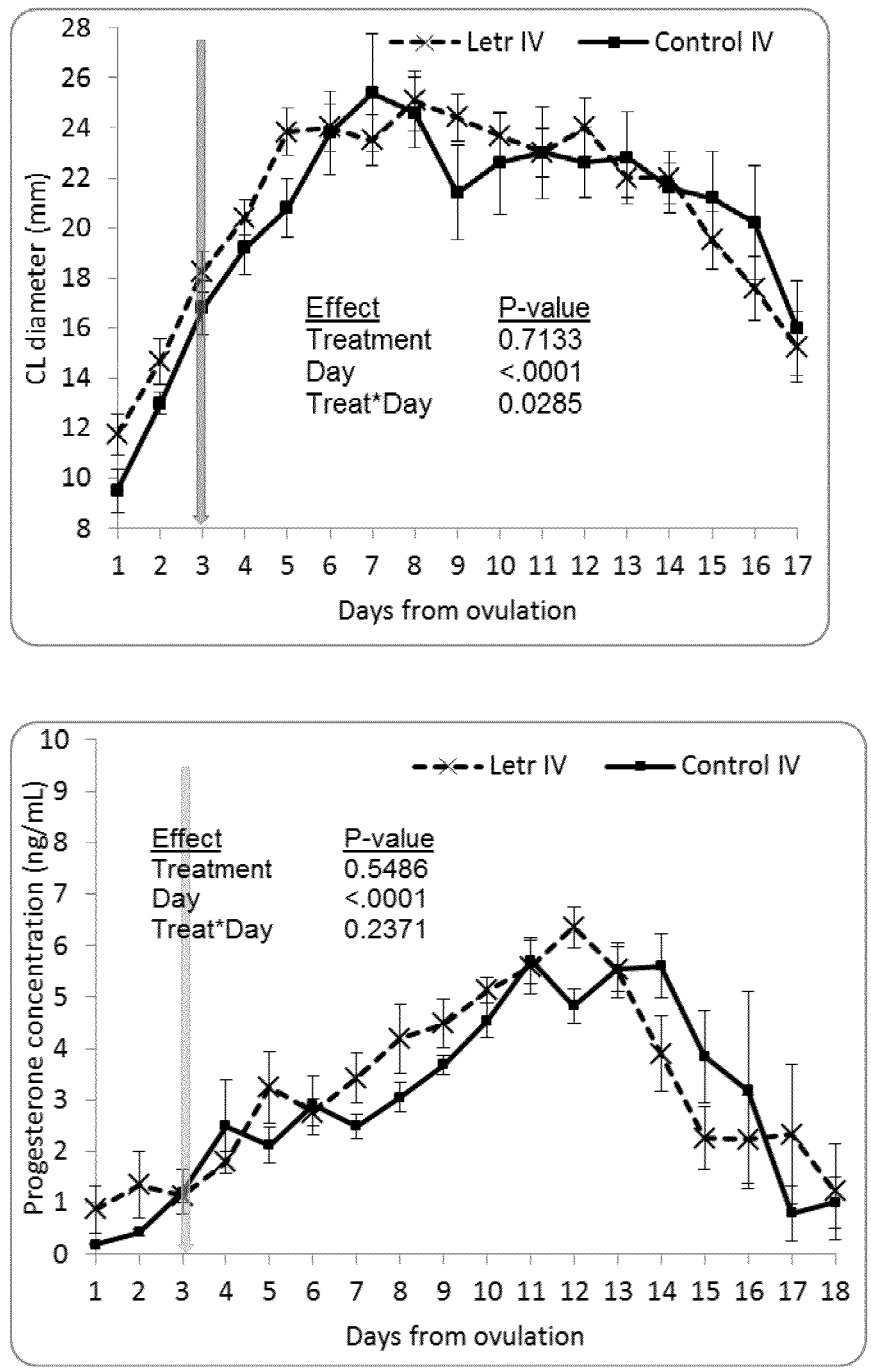
Figure 20:
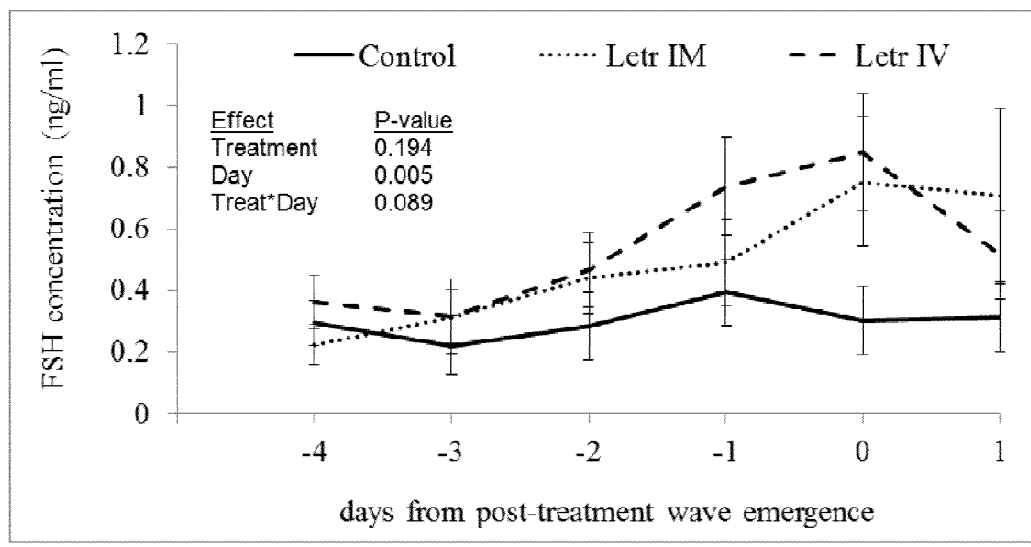
Figure 20:
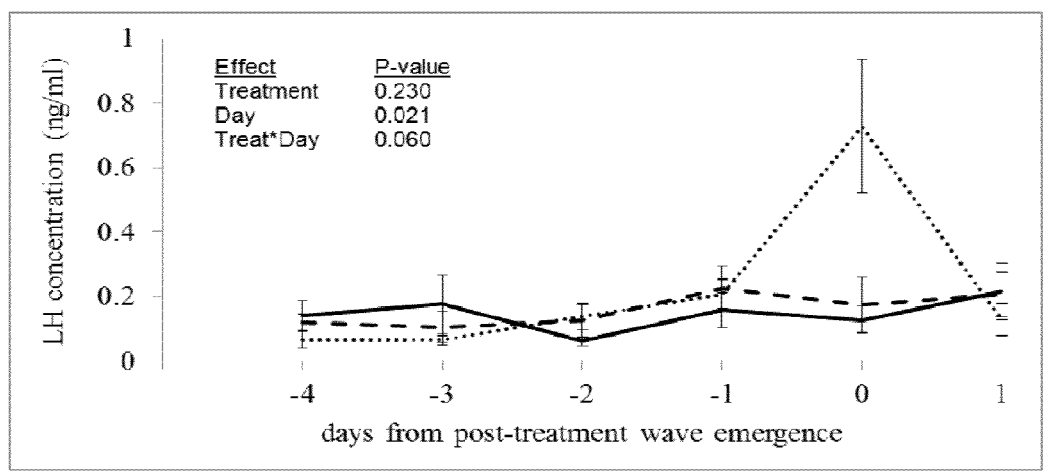

FIG. 16 is a line graph depicting dominant follicle diameter profile (dominant follicle diameter profile in heifers treated with letrozole or placebo given intramuscularly or intravenously on Day 3 post wave emergence. Arrow indicates day of treatment.);

FIG. 17(a) is a line graph depicting CL diameter profile in heifers treated with letrozole or placebo given intramuscularly on Day 3 post wave emergence;

FIG. 17(b) is a line graph depicting plasma progesterone concentration in heifers treated with letrozole or placebo given intramuscularly on Day 3 post wave emergence;

FIG. 18 are line graphs depicting CLL diameter and progesterone concentration;

FIG. 19 are line graphs depicting CLL diameter and progesterone concentration;

FIG. 20 are line graphs depicting FSH and LH concentrations.

Figure 21:
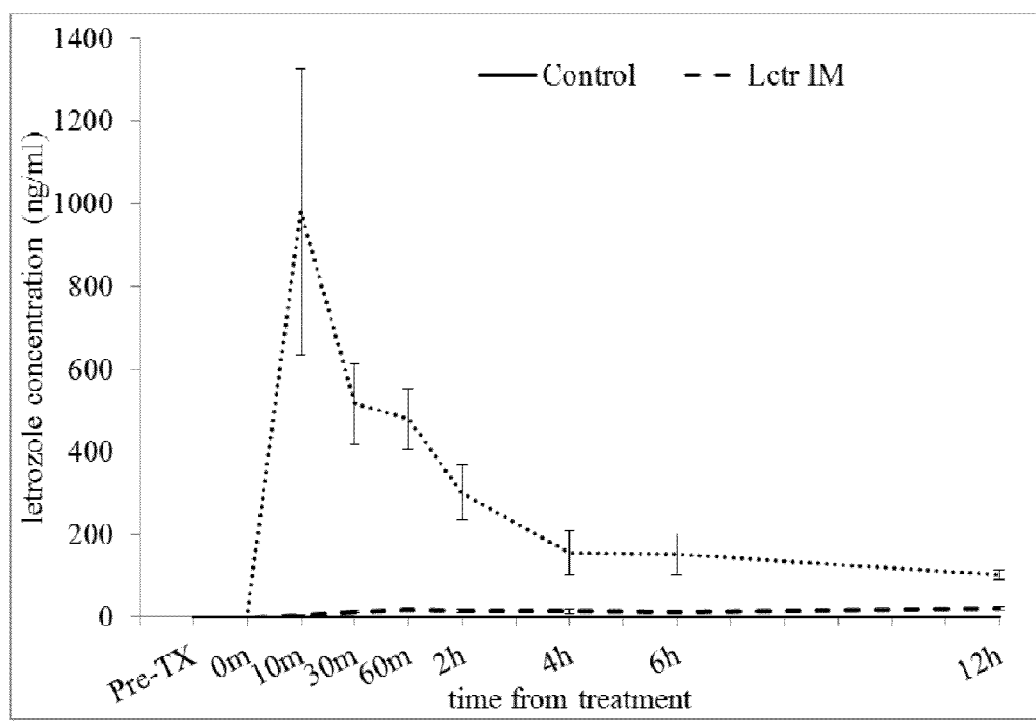
Figure 22:
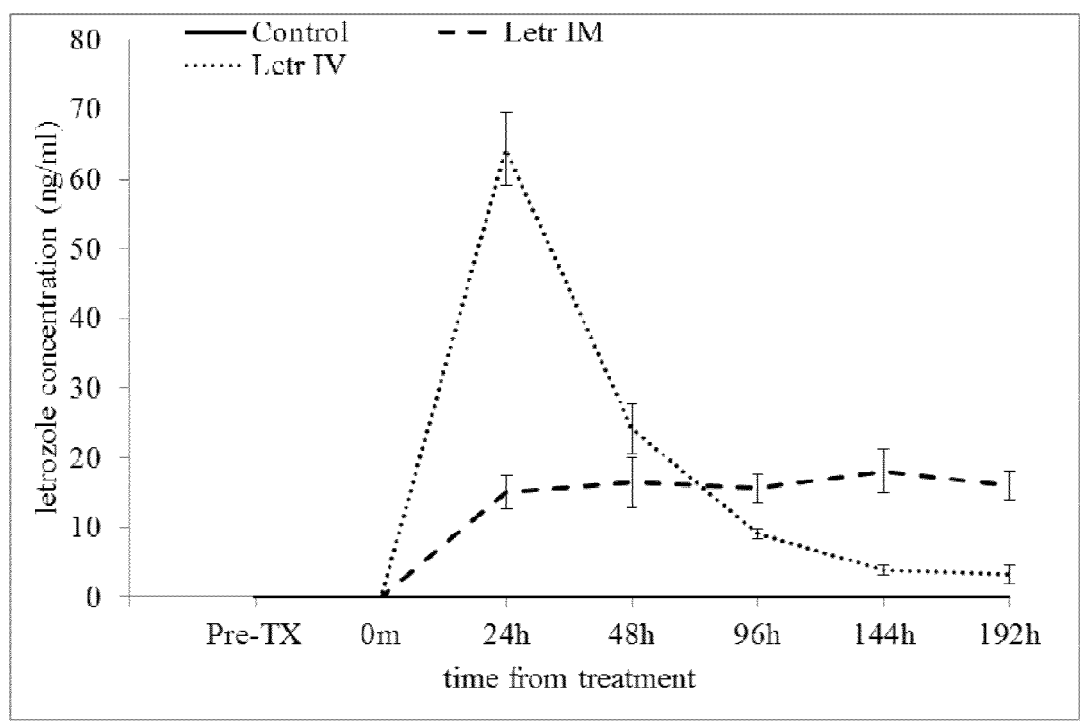
Figure 23:
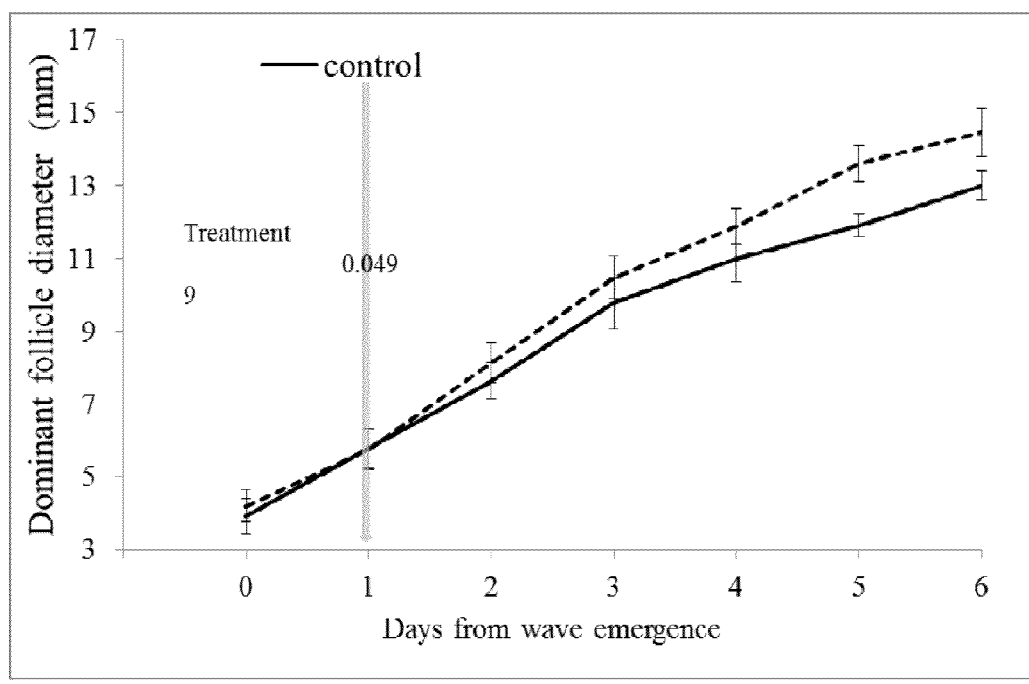
Figure 25:
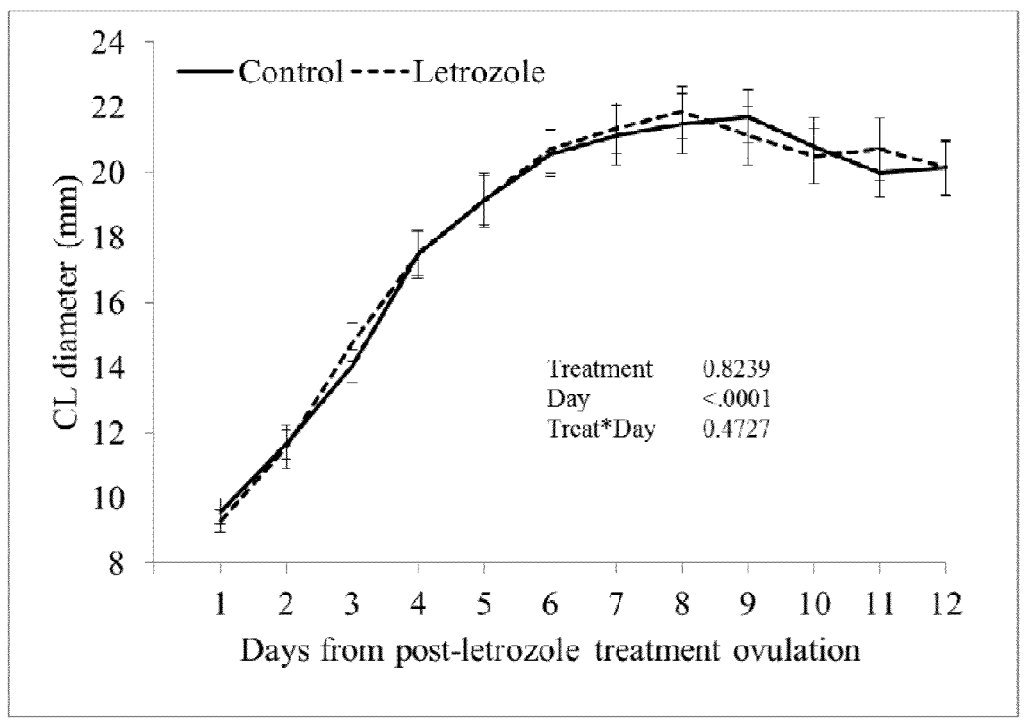
Figure 26:
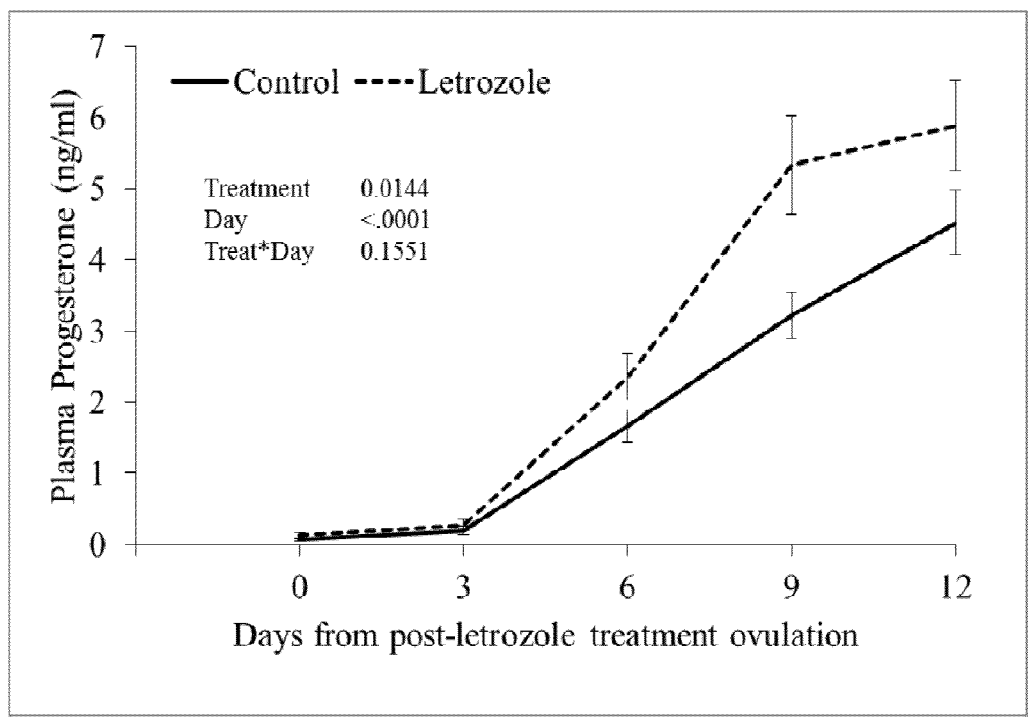

FIG. 21 is a line graph depicting letrozole concentration;

FIG. 22 is a line graph depicting letrozole concentration;

FIG. 23 is a line graph depicting dominant follicle diameter;

FIG. 24 is a table;

FIG. 25 is a line graph depicting CL diameter;

FIG. 26 is a line graph depicting plasma progesterone; and

Figure 27:
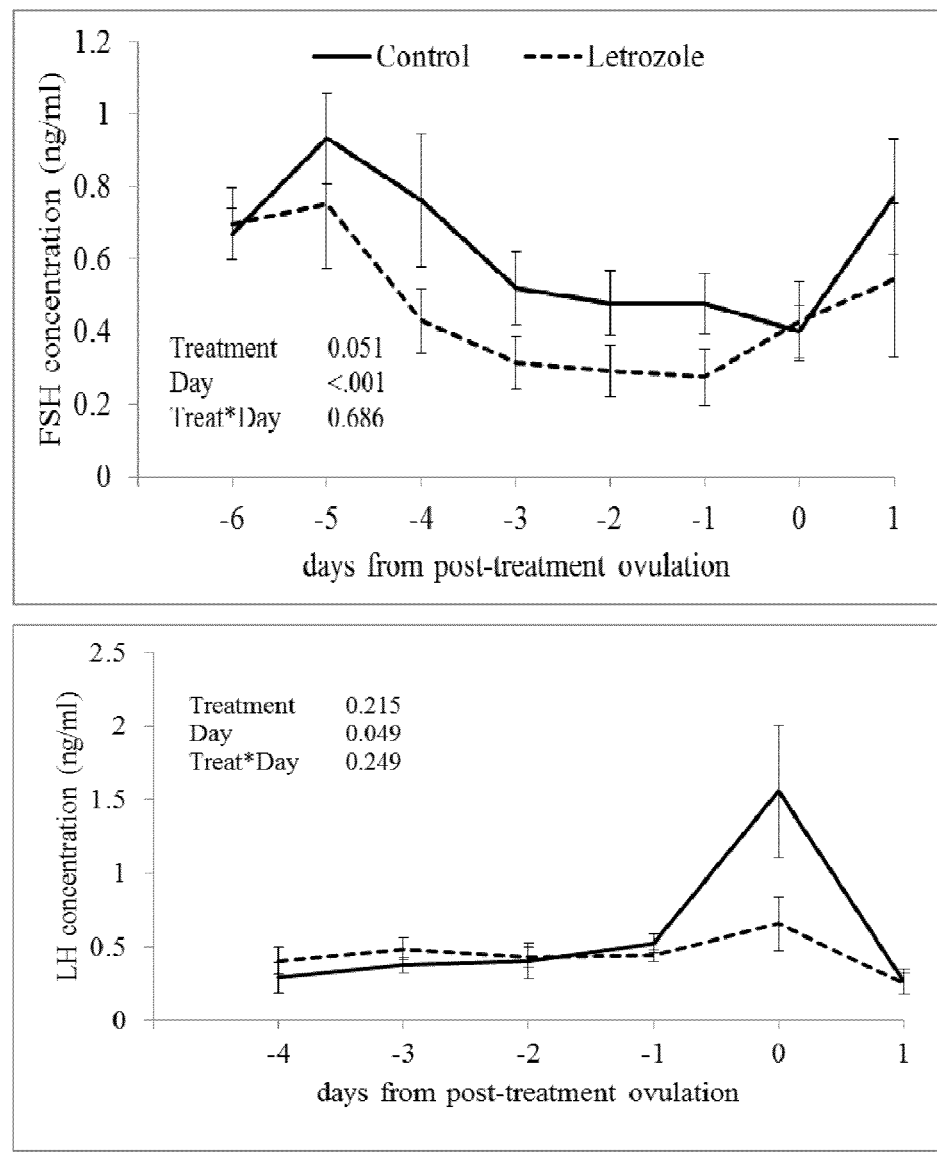

FIG. 27 are line graphs depicting FSH and LH concentrations.

In the Detailed Description that follows, the numbers in bold face type serve to identify the component parts that are described and referred to in relation to the drawings depicting various embodiments of the invention. It should be noted that in describing various embodiments of the present invention, the same reference numerals have been used to identify the same of similar elements. Moreover, for the sake of simplicity, parts have been omitted from some figures of the drawings.

DETAILED DESCRIPTION

As will be described in more detail below, the present invention relates to the use of an aromatse inhibitor compound(s), and to a pharmaceutical composition(s), comprising the aromatase inhibitor compound for use in synchronizing ovulation in a herd, inducing superovulation in a single animal; and improved frequency of successful implantation and development of fertilized ova.

The methods of the present invention are suitable for use in female mammals

In some examples, mammals are humans, non-human primates, companion animals (such as dogs, cats, and the like), live stock (such as cows, horses, pigs, and the like).

In a specific embodiment, methods of the present invention are suitable for use in bovids, including heifers, dairy cows, and beef cattle.

In another specific embodiment, methods of the present invention are suitable for use in Equidae, including horses.

The term "herd", as used herein refers to at least two mammals.

Estrogens are produced by the conversion of androgen through the activity of aromatase; the suppression of estrogen biosynthesis can be achieved by specifically inhibiting the aromatase enzyme.

Estrogens have also been used by the beef industry as growth promoters, in part because of the role they play in other important physiological functions in vertebrates such as determination of secondary sexual characteristics, linear growth and closure of epiphyseal plates, and fat deposition. As noted above, however, use of natural or synthetic estrogens in food producing animals is increasingly undesirable.

Aromatase inhibitors have been classified as first-, second- and third-generation inhibitors according to the chronologic order of their clinical development and as type 1 or type 2 inhibitors according to their mechanism of action. Type 1 aromatase inhibitors are generally steroidal analogues of androstenedione that bind irreversibly to aromatase (non-competitive, irreversible), thereby inactivating the enzyme. Type 2 aromatase inhibitors are generally nonsteroidal and bind reversibly to the heme group of the enzyme by way of a basic nitrogen (competitive, reversible).

As used herein, "aromatase inhibitors" refers to substances that inhibit the enzyme aromatase (estrogen synthetase), which is responsible for converting androgens to estrogens. Aromatase inhibitors may have a non-steroidal or a steroidal chemical structure.

In one aspect of the present invention, the aromatase inhibitor used is a non-steroidal aromatase inhibitor. Examples of non-steroidal aromatase inhibitors include letrozole, fadrozole and anastrozole. In a specific example the non-steroidal aromatase inhibitor is letrozole.

The term "non-steroidal aromatase inhibitor" as used herein refers to both a single non-steroidal aromatase inhibitor or a mixture of more than one non-steroidal aromatase inhibitor.

The methods of the present invention include compounds that have been used in artificial insemination protocols in cattle, including gonadotropin-releasing hormone, progesterone, melengestrol, prostaglandin F2α (dinoprost, PGF) and cloprostenol.

A summary of drug products approved in the USA for synchronization of estrous in cattle are as follows:

| Active or co-active ingredient | Number of products approved |
| --- | --- |
| Cloprostenol Sodium | 2 |
| Progesterone | 2 |
| Melengestrol Acetate | 6 |
| Dinoprost Tromethamine | 3 |
| Norgestomet | 1 |
| Estradiol Valerate | 1 |

Gonadotropin releasing hormone (GnRH), is a decapeptide that is secreted by the hypothalamus into the hypophyseal portal circulation in response to neural and/or chemical stimuli, causing the biosynthesis and release of luteinizing hormone (LH) and follicle-stimulating hormone (FSH) by the pituitary. GnRH is also known as gonadoliberin, LH releasing hormone (LHRH), FSH releasing hormone (FSHRH) and LH/FSH releasing factor (LH/FSHRF).

Prostaglandins are generally characterised by the substituents on the cyclopentyl ring. The 2α prostaglandins and prostaglandin analogues generally have two hydroxyl groups in a cis configuration relative to the cyclopentane ring, and two side chains in a trans configuration relative to each other, each side chain having one double bond. Analogues of PGF2α can have a different number of double bonds in the side chains, and the substituents along the side chains may vary. Additionally, in some PGF2α analogues, the side chain carboxylic acid group may be esterified.

Additional analogues of prostaglandin $F_2\alpha$ include fenprostalene ((.+-.)-9α11α15α-trihydroxy-16-phenoxy-17,18,19,20-tetranorprosta-4,5,13-trans-trienoic acid methyl ester); cloprostenol (7-[2-[4-(3-chlorophenoxy)-3-hydroxy-1-butenyl]-3,5-dihydroxycyclopentyl]-5-heptenoic acid), an aryloxymethyl analog of prostaglandin $F_2\alpha$; fluprostenol (9,11,15-trihydroxy-15-methylprosta-4,5,13-trien-1-oic acid methyl ester; prostalene (7-[3-hydroxy-2-(3-hydroxy-1-octenyl)-5-oxocyclopentyl]-5-heptenoic acid); alfaprostol ([1R-[1.alpha.(Z), 2β(S*), 3β,5α]]-7-[2-(5-cyclohexyl-3-hydroxy-1-pentynyl)-3,5-dihydroxyc yclopentyl]-5-heptenoic acid methyl ester); and the pharmaceutically acceptable salts of prostaglandin, e.g., the tromethamine salt of prostaglandin $F_2\alpha$. (dinoprost tromethamine), and its analogs. The pharmaceutically acceptable salts thereof include, but are not limited to, the addition salts of inorganic and organic acids, which are commercially available, such as the tromethamine and sodium salts.

A specific example of the present invention, the analogue of prostaglandin is cloprostenol.

As used herein, the term "prostaglandin" refers to any prostaglandin or prostaglandin analog, which is either naturally occurring or synthetically produced, and which has and/or exerts the desired characteristic in use.

The compound(s) and composition(s), pharmaceutically acceptable salts and prodrugs of the present invention are administered to an animal using a method that delivers a compound of this invention systemically and/or locally.

Examples of methods of administration include parenteral administration, oral administration, topical administration, vaginal administration, and the like.

As used herein, "topical administration" includes cream, ointment or spray applied to the skin.

As used herein, the term "parenteral" includes intravenous, subcutaneous, intramuscular, transdermal, intradermal, intraorbital, ophthalmic, intraventricular, intracranial, intracapsular, intraspinal, intracisternal, intraperitoneal, topical, intranasal, aerosol, scarification, and buccal administration. Also encompassed is intramammary injection where a suspension or solution is introduced into the udder via the teat.

Parenteral administration may include, but is not limited to, sterile solutions which may also contain buffers, diluents and/or carriers, as known by the skilled worker. For example, sterile aqueous solutions of the corresponding water-soluble salts may be used. Such aqueous solutions may be suitably buffered, if necessary, and the liquid diluent first rendered isotonic with sufficient saline or glucose.

Examples of carriers include solutions, solvents, dispersion media, delay agents, emulsions and the like. For example, alcohols, glycols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxymethyl cellulose, polyvinyl pyrrolidine, etc. The pharmaceutical preparations can be sterilized, and, if desired, mixed with auxiliary agents, including lubricants, preservatives, stabilizers, wetting agents, emulsifiers, salts for influencing osmotic pressure, buffers, coloring. Solutions, suspensions, emulsions, or implants, can conveniently be provided for appropriate administration. The use of such carriers for pharmaceutically substances are well known in the art.

As used herein, "oral administration" includes administering the constituents of the combined preparation in a suitable oral form such as, e.g., tablets, capsules, suspensions, solutions or emulsions, powders, syrups, granules or pellets for admixture with feedstuffs; pastes for application to the tongue, and the like.

As used herein, "vaginal administration" includes vaginal administration presented as pessaries, tampons, creams, gels, pastes, foams or spray formulations. Vaginal administration may also occur using an intravaginal device. For example, as a time release composition can be used, as is well known to those skilled in the art.

As used herein, "pharmaceutically acceptable" includes the carrier, diluent, excipients, and/or salts or prodrugs, and must be compatible with the other ingredients of the formulation, and not deleterious to the patient.

As used herein, "prodrug" refers to a compound that is transformed in vivo to yield a compound of the present invention. The transformation may occur by various mechanisms, such as through hydrolysis in blood As used herein, "pharmaceutically acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluene-sulfonate. The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methyl-glucamine), benethamine (N-benzylphenethylamine), piperazine or tromethamine (2-amino-2-hydroxymethyl-1,3-propanediol).

As noted above, the methods of the present invention relate to use of an aromatase inhibitor compound(s) and to a pharmaceutical composition(s) comprising the aromatase inhibitor compound for use in synchronizing ovulation in a herd, inducing superovulation in a single animal; improved frequency of successful implantation and development of fertilized ova, and twinning. In a specific example, the aromatase inhibitor is the non-steroidal aromatase inhibitor Letrozole.

In one embodiment of the present invention, letrozole is used in the synchronization of ovulation of members of a herd of cattle, so as to enable timed insemination of the members of the herd.

The term "insemination" as used herein, refers to introducing semen by any method known in the art, including, but not limited to, natural and artificial insemination.

In one example, a slow-release device containing letrozole may be applied on random days of the estrous cycle to induce the formation of a persistent dominant follicle and delay wave emergence by preventing spontaneous ovulations (i.e., inhibiting the pre-ovulatory rise in estradiol and potentially delaying luteolysis). On Day 5 (Day 0=day of device insertion), a luteolytic dose of PGF is given to induce regression of the corpus luteum (CL), followed on Day 7 by an ovulatory dose of GnRH or pLH to synchronize ovulation. Insemination (e.g., artificial insemination) at detected estrus or following treatment with GnRH or pLH on Day 6 or 7 to synchronize ovulation (fixed-time artificial insemination [FTAI] on Day 7-7.5).

In another example, a prostaglandin such as Lutalyse is administered (e.g., about 5 mL Lutalyse® administered intramuscularly) followed (i.e., 48 h) by administration of Letrozole (i.e., 1-2 mg/Kg, intravenously) to synchronize individual cows of a herd with respect to the time of occurrence of estrus, ovulation, or both.

In another example, a letrozole containing device may be given prior to the initiation of a 5-day Ovsynch protocol so as to increase the ovulation rate on the first GnRH treatment and therefore the total synchrony achieved at the day of artificial insemination.

For the purposes of ovarian superovulation and embryo transfer, superstimulatory treatments may be initiated 36 to 48 hours after letrozole and GnRH/pLH treatment, as outlined in paragraph 49 above.

In another example of superovulation, Letrozole is administered (i.e., 1-2 mg/Kg, IV, SID for 4 days or a slow-release device containing letrozole) at the beginning of follicular wave emergence in a cow, concurrent with a conventional superstimulatory treatment protocol that is also initiated at wave emergence.

In the case of mares, in the present application, treatment with letrozole (1-2 mg/Kg, IV, SID for 4 days or a slow-release device containing letrozole) may be applied on random days of the estrous cycle to induce the formation of a persistent dominant follicle and delay wave emergence by preventing spontaneous ovulations (i.e., inhibiting the pre-ovulatory rise in estradiol and potentially delaying luteolysis). On Day 5 (Day 0=day of treatment), a luteolytic dose of PGF is given to induce regression of the corpus luteum (CL), followed on Day 7 by an ovulatory dose of GnRH or pLH to synchronize ovulation. Insemination (e.g., artificial insemination) at detected estrus or following treatment with GnRH or pLH on Day 6 or 7 to synchronize ovulation (fixed-time artificial insemination [FTAI] on Day 7-7.5).

In another embodiment, there is provided a method for improving fertility. Letrozole treatment, given in early metestrus (about Day 1 post-ovulation) or mid-diestrus (about Day 9 post-ovulation) resulted in a luteotrophic effect, documented by larger CL diameter and greater plasma progesterone profiles in treated animals. Treatment during the early luteal phase increases CL viability and progesterone production, which is important for ensuring rapid growth of a healthy embryo and successful establishment of pregnancy. In high-producing dairy cows, for example, low levels of progesterone account for low pregnancy rates and high embryonic loss rates. Letrozole, (1-2 mg/Kg, IV, SID for 4 days or a slow-release device containing letrozole), is given one day after artificial insemination to promote development of the CL, resulting in a larger CL diameter and higher circulating concentrations of progesterone.

Similarly, letrozole treatment may be given so that its effect encompasses the period of maternal recognition of pregnancy (i.e., the time of luteal response to pregnancy). In cattle, letrozole treatment is initiated on or before 15 days after artificial insemination (maternal recognition of pregnancy is between Days 15 and 17 post-ovulation in cattle). Treatment at this time will promote the establishment of pregnancy through two mechanisms. Firstly, letrozole exerts a luteotrophic effect to enhance CL functionality and survival. Secondly, letrozole will compromise the luteolytic mechanism by decreasing circulating estradiol concentration which mediates the luteolytic process by stimulating the expression of oxytocin receptors in the endometrium, which are necessary for prostaglandin production and release. Again, this is a common problem in high producing dairy cattle; low levels of progesterone result in insufficient trophoblast expansion to block prostaglandin production and release from the uterus.

For embryo transfer recipients—letrozole treatment is initiated prior to ovulatory follicular wave emergence to induce co-dominance, and double ovulation. Letrozole (250 μg/kg/day) is given from Day 1 (Day 0=wave emergence) until Day 7. PGF is administered on day 5 followed by GnRH/LH treatment 36 h later. As a result, recipient animals will have more than one corpus luteum and higher progesterone levels to ensure a successful attachment and development of the transferred embryo. An alternative protocol for embryo transfer recipients is letrozole treatment, in a slow-release preparation, initiated one day after ovulation for 5 days to promote development of the new CL, resulting in a larger CL diameter and higher circulating concentrations of progesterone.

In another embodiment there is provided a method of improved twinning. As shown herein, letrozole treatment given before dominant follicle selection, induces the development of co-dominance; i.e., 2 dominant follicles. The data suggest that letrozole may be used to produce double ovulations and twin pregnancies with much higher efficiency than other previously explored treatments (e.g., eCG or FSH). The advantage of letrozole treatment is that it appears to induce the development of only two dominant follicles, which overcome the adverse effects of gonadotropin treatments where multiple (3 to 10) ovulations and conceptions commonly occur. In this regard, a letrozole-impregnated slow-releasing device may be applied on the day of or the day after follicle wave emergence of either an anovulatory or ovulatory follicular wave. On Day 5 after wave emergence, the letrozole device is removed and a luteolytic dose of PGF given. Artificial insemination at detected estrus or following treatment with GnRH or pLH on Day 6 or 7 to synchronize ovulation (FTAI) would be expected to result in twin pregnancies.

Inducing multiple ovulation in mares is difficult and expensive. Letrozole treatment (as described in paragraph 53 above) may be used in mares, with or without other superstimulatory hormones (e.g., FSH or equine pituitary extract), to induce multiple ovulation in mares for the purposes of embryo production and embryo transfer.

To gain a better understanding of the invention described herein, the following examples are set forth. It should be understood that these example are for illustrative purposes only. Therefore, they should not limit the scope of this invention in any way.

EXAMPLES

Example I

Materials and Methods

Cattle

Hereford-cross beef heifers, 14 to 20 months of age and weighing between 295 and 450 kg, were chosen from a herd of 50 heifers maintained in outdoor corrals at the University of Saskatchewan Goodale Research Farm (52° North and 106° West). Heifers were fed alfalfa/grass hay and grain to gain approximately 1.3 Kg per day and had water ad libitum during the experimental period from July to October. Heifers were initially examined by transrectal ultrasonography (7.5 MHz linear-array transducer, Aloka SSD-900; Tokyo, Japan) to confirm that they were postpubertal by observing the presence of a CL [33].

Treatments and Examinations

Heifers in which a CL was detected during the initial examination were given 500 of cloprostenol (PGF, Estrumate™, Schering-Plough Animal Health, Pointe-Claire, QC, Canada) intramuscularly (im) to induce regression of the CL and to synchronize ovulation [34]. Heifers were examined daily by transrectal ultrasonography to detect ovulation. Transvaginal ultrasound-guided follicular aspiration of follicles ≥5 mm was performed five to eight days after ovulation to synchronize wave emergence [35]. Heifers were examined daily by transrectal ultrasonography to detect follicular wave emergence, which was expected 1 to 1.5 days after follicular ablation [35]. Four days after follicular ablation (approximately 2.5 days after follicular wave emergence), and at the time follicular dominance becomes apparent [36], heifers were assigned randomly to the following treatment groups and given a single intravenous dose of 1) 500 μg/kg of letrozole (high dose group, n=9), 2) 250 μg/kg of letrozole (medium dose group, n=10), 3) 125 μg/kg of letrozole (low dose group, n=10), or 4) 20 ml of phosphate buffered saline (PBS control group, n=10). For practical purposes, the dose of letrozole was calculated based on an average weight of 400 kg for all heifers. The average oral dose used in women (2.5-5 mg per day for 5 days) was used to estimate the medium dose for cattle [29, 30]. The high and low doses were set as double and half the medium dose, respectively. The day of treatment was defined as Day 0. For intravenous injection, letrozole was prepared in 95% ethanol at a final concentration of 5 mg per ml, resulting in an injection volume of 10-40 ml. The experiment was performed in four replicates (n=2-3 per group per replicate) and each heifer was used only once.

Ovarian Ultrasonography

The observations from ultrasound examination were recorded on a sketch sheet in which each ovary and its structures (CL and follicles ≥4 mm in diameter [37]) were represented in size and location. Ovulation was defined as the disappearance of any follicle ≥8 mm between two consecutive daily examinations, and was confirmed by the subsequent development of a CL [33]. Follicular wave emergence was defined retrospectively as the day when the dominant follicle was first identified at a diameter of 4 or 5 mm [36, 38]. If the dominant follicle was not identified until it reached 6 or 7 mm, the previous day was considered day of the follicular wave emergence [39]. The dominant follicle of a wave was defined as the largest antral follicle of that wave after deviation, and the first subordinate follicle as the second largest antral follicle of that wave [40]. The day of onset of follicular and luteal regression was defined as the first day of an apparent constant decrease in follicular and luteal diameters, respectively [36].

Collection of Blood Samples

Blood samples were collected by jugular or coccygeal venipuncture into 10 ml heparinized vacuum tubes (Becton Dickinson Vacutainer Systems, Franklin Lakes, N.J., USA). Blood samples were collected at 0, 0.25, 0.5, 1, 1.5, 2, 3, 4, 6, 8, 12, 24, 36, 48 hours post-treatment [41] using an indwelling jugular catheter as previously described [42] and daily thereafter to the first post-treatment ovulation. Blood samples were centrifuged at 1500×g for 20 minutes; plasma was separated and stored in plastic tubes at −20° C.

Hormone Assays

Plasma LH concentrations were determined in duplicate using a double-antibody radioimmunoassay (NIDDK-bLH4) [5, 43]. The minimum and maximum values along the standard curve were 0.06 and 8 ng/mL, respectively. The intra- and inter-assay coefficients of variation were 10.2% and 8.8%, respectively, for low reference samples (mean, 0.88 ng/mL) and 9.4% and 9.1%, respectively, for high reference samples (mean, 2.7 ng/mL).

Plasma FSH concentrations were determined in duplicate using a double-antibody radioimmunoassay using NIDDK-anti-oFSH-1 primary antibody and expressed as USDA bovine FSH-I1 units [5, 43]. The minimum and maximum values along the standard curve were 0.12 and 16 ng/mL, respectively. The intra- and inter-assay coefficients of variation were 11.2% and 10.0%, respectively, for low reference samples (mean, 1.7 ng/mL) and 12.0% and 12.4%, respectively, for high reference samples (mean 4.4 ng/mL).

Plasma estradiol concentrations were determined in duplicate by enzyme-linked immunosorbent assay (Cayman Chemical Company, Ann Arbor, Mich., USA). In this competitive ELISA, plasma steroid competes with acetylcholinesterase-labelled steroid for the binding site on polyclonal rabbit anti-steroid antibody. The antiserum to estradiol was reported to cross-react with estradiol-3-glucoronide (14%), estrone (12%), and estriol (0.3%). For all other steroid hormones, cross-reactivity was reported as <0.1%. The minimum and maximum values along the standard curve were 6.6 and 4000 pg/well, respectively. The intra- and inter-assay coefficients of variation were 11.7% and 12.7%, respectively, for reference samples analyzed in duplicate. A concentration procedure using diethyl ether extraction was performed prior to the assay in all samples to increase estrogen concentration to measurable levels [44]. A $^3$H-labeled steroid was added to each plasma sample before extraction as an internal recovery standard. After the extraction procedure, a fraction of the final extract was quantified in a liquid scintillation counter to test for recoveries [45].

Plasma Letrozole Concentration

Plasma concentrations of letrozole were determined using high performance liquid chromatography tandem mass spectrometry (LC/MS/MS). To extract letrozole from the samples, 250 µL of a buffer solution (0.1M ammonium) were added to 250 µL of plasma followed by the addition of 5 mL of methyl t-butyl ether (MTBE) and vortexed for 15 seconds. The organic layer was removed by pipetting and transferred to a fresh 15 mL plastic tube. This second tube was dried by gentle nitrogen gas flow. The dried extract was reconstituted in 1 mL of 100% ethanol, sonicated for 5 minutes and transferred to a labelled vial for further analysis. Separation was accomplished by HPLC (Agilent 1200, Santa Clara, Calif., USA) fitted with an analytical column (50×2.1 mm, 3 µm particle size; Thermo Scientific Betasil C18, Waltham, Mass., USA) operated at 35° C. Gradient conditions were used at a flow rate of 250 µL/min, starting at 85% A (0.1% acetic acid) and 15% B (0.1% acetic acid in acetonitrile). Initial conditions were held for 2 min and then ramped to 100% B at 6 min, held until 9 min, decreased to 0% B at 11 minutes, and returned to initial conditions at 13 minutes, and held constant until 15 minutes. Mass spectra were collected using a tandem mass spectrometer (Applied Bioscience SCIEX 3000, Foster City, Calif., USA) fitted with an electrospray ionization source, operated in the negative ionization mode. Chromatograms were recorded using multiple reaction monitoring (MRM) mode, where at least two transitions per-analyte were monitored. The following instrument parameters were used: desolvation temperature 450° C., desolvation (curtain) gas 6.0 arbitrary units (AU), nebulizer gas flow 4 AU, ion spray voltage 4500 V, collision gas 12 AU, collision energy 46 AU, declustering potential 30 AU, and a dwell time of 100 msec. Quantification using these transitions was performed using Analyst 1.4.1 software provided by SCIEX (Applied Bioscience, Foster City, Calif., USA). The minimum and maximum values along the standard curve were 025 and 500 µg/mL respectively. The limit of quantification used in this method was 250 ng/L and the mean recovery was 70%. The plasma letrozole concentration vs. time (C-t) data for each heifer was analyzed by non-compartmental techniques using a computer modeling program (WinNonLin Standard Edition Version 2.1, Pharsight Corporation, Mountain View, Calif., USA). Peak concentration in plasma (Cmax) and time to peak concentration (tmax) were determined using observed values. The apparent terminal rate constant ($\lambda$) was determined by linear regression of the last 6-8 points on the terminal phase of the logarithmic plasma concentration vs. time curve. The area under the C-t curve until the final plasma sample (AUClast) was determined using the linear trapezoidal rule. The total area under the curve extrapolated to infinity (AUC0-∞) was calculated by adding the Clast obs/$\lambda$+AUClast. The terminal half-life (T1/2$\lambda$) was calculated as ln2/$\lambda$. The mean residence time (MRT) was calculated as the area under the moment curve extrapolated to infinity (AUMC0-∞)/AUC0-∞. Systemic clearance (CIS) was determined using the dose divided by AUC0-inf. The apparent volume of distribution (V$\lambda$/f) was calculated by clearance divided by $\lambda$.

Statistical Analyses

Statistical analyses were done using the Statistical Analysis System software package (SAS Learning Edition 9.1, 2006; SAS Institute Inc., Cary, N.C., USA). Time-series hormone data, plasma letrozole concentration, and follicular diameter profiles were analyzed by repeated measures, using the PROC MIXED procedure. The main effects were treatment (high, medium and low dose, and control), time, and their interactions. When no differences were detected among doses of letrozole, data were combined and re-analyzed as a single letrozole treatment group. Single point measurements (intervals from ablation to wave emergence, treatment to wave emergence, treatment to ovulation, treatment to onset of follicular regression, and treatment to onset of CL regression) were analyzed by one-way analysis of variance. Paired t-test was used to compare estradiol concentration pre- and post-treatment within a treatment group and two-sample t-test was used to compare estradiol concentration at a single data point between letrozole and control groups. An F-test was used to analyse if the variability in the interval from treatment to wave emergence was significantly different between letrozole-treated and control heifers. Due to individual variability in circulating concentrations of LH and FSH among heifers, and because our objective was to determine the effect of treatment within individuals, LH and FSH data were transformed to a percentage of the mean concentration of the first three samples (i.e., 0, 15, and 30 minutes post-treatment) for each individual heifer. Residuals from percent data were normally distributed, therefore, transformation of percent data was not required. All values are expressed as mean±SEM.

Animal procedures were performed in accordance with the Canadian Council on Animal Care and were approved by University of Saskatchewan Protocol Review Committee.

Results

The interval from follicular ablation to emergence of the new follicular wave did not differ among treatment groups (1.7, 1.6, 1.7 and 1.6 days for high-, medium- and low-dose letrozole, and control groups, respectively). Consequently, treatment was applied 2.4±0.1 days after follicular wave emergence, when the growing dominant follicle was 7.1±0.3 mm. The interval from ablation to treatment, and the diameter of the dominant follicle at the time of treatment did not differ among groups.

Figure 1:
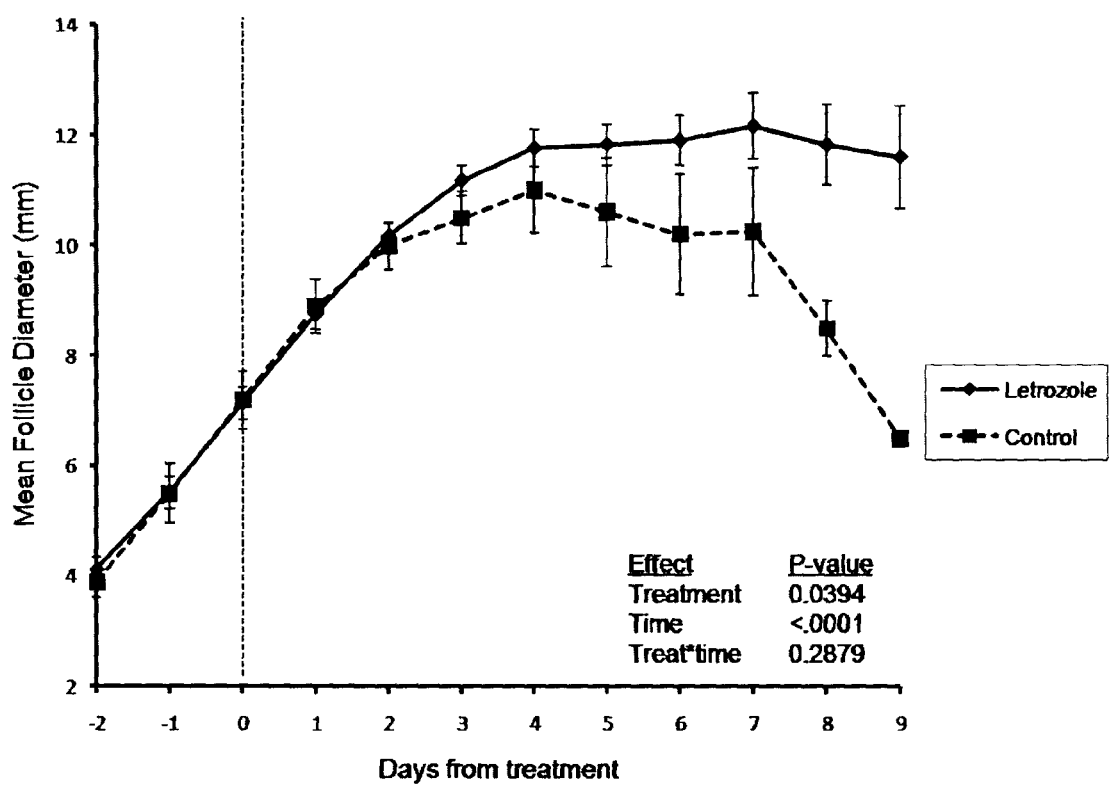
FIG. 1 is a line graph depicting the diameter profile of the dominant follicle in heifers treated with letrozole (diameter profile (mean±SEM) of the dominant follicle in heifers treated with letrozole (high-, medium- and low-dose groups combined; n=29) 4 days after follicular ablation (i.e., 2.5 days after wave emergence), compared to saline-treated controls (n=10))

Although the dominant follicle diameter profiles after letrozole treatment followed a dose-dependent pattern, differences among the letrozole dose groups were not significant (P=0.11, FIG. 14). Therefore, data from all letrozole dose groups were combined for comparison with the control group. The dominant follicle diameter profile of letrozole-treated heifers was larger (P<0.04) than that of control heifers (FIG. 1). The dominant follicle grew to a larger diameter (11.0±0.32 vs 9.7±0.55 mm) and regressed later (P<0.05; Table 1) in letrozole-treated heifers with than in control heifers.

The number of heifers in which the extant dominant follicle (i.e., the dominant follicle present at the time of treatment) ovulated did not differ among groups (5/9, 5/10, 7/10 and 4/10 heifers in high-, medium-, low-dose and control groups, respectively), but the interval to ovulation was longer in letrozole-treated heifers compared to controls (Table 1). In heifers that did not ovulate the extant dominant follicle, the intervals from treatment to onset of dominant follicle regression and to emergence of a new follicular wave were longer in those treated with letrozole than in controls (P<0.05; Table 1). The variability (degree of synchrony) in intervals from treatment to wave emergence or dominant follicle regression was not different between letrozole-treated and control groups (F-value=2.7, P>0.05).

TABLE 1

Effects of letrozole on interval to follicle wave emergence, ovulation, onset of follicular regression and onset of CL regression in cattle. Data from low-, medium- and high-dose treatment groups were combined, and compared to saline-treated controls. Values are expressed as mean ± SEM.

| Intervals (days) | Letrozole | Control |
|---|---|---|
| Treatment to wave emergence* | $7.5 \pm 0.27^a$ (n = 29) | $5.9 \pm 0.46^b$ (n = 10) |
| Treatment to ovulation of extant dominant follicle** | $9.0 \pm 0.42^a$ (n = 16) | $8.0 \pm 0.86^a$ (n = 4) |
| Treatment to onset of regression of extant dominant follicle** | $8.7 \pm 0.47^a$ (n = 13) | $5.2 \pm 0.65^b$ (n = 6) |
| Treatment to onset of CL regression | $6.1 \pm 0.35^a$ (n = 29) | $5.1 \pm 0.62^a$ (n = 10) |

Figure 3:
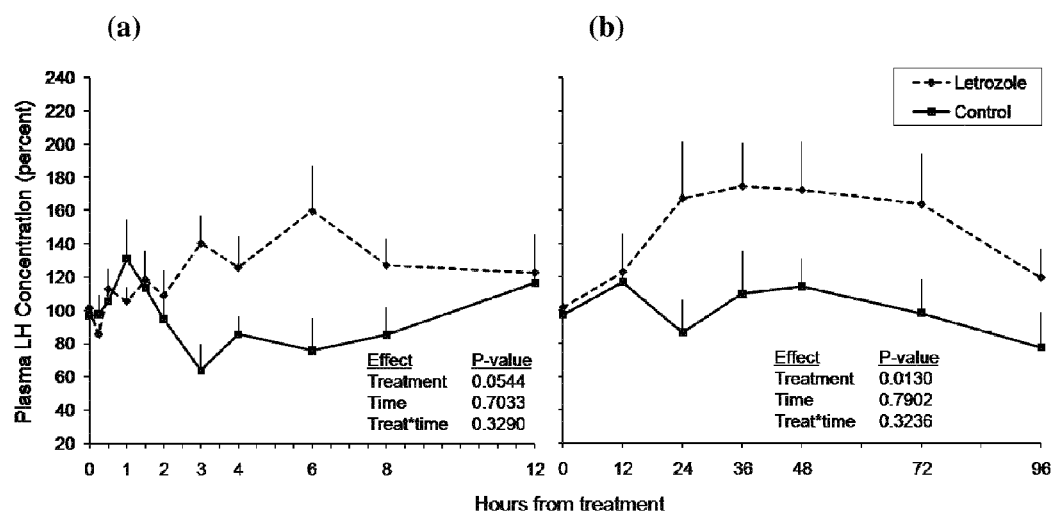
FIG. 3($a$) is a line graph depicting plasma LH concentrations in heifers after a single intravenous dose of letrozole (plasma LH concentrations in heifers (percent change after treatment; mean±SEM) during the first 12 hours after a single intravenous dose of letrozole (high-, medium- and low-dose groups combined; n=29) given 4 days after follicular ablation (i.e., 2.5 days after wave emergence), compared to saline-treated controls (n=10))

$^{ab}$Within rows, values with different superscripts are different (P < 0.05)
*Differences in variability between groups were not significant
**Dominant follicle present at the time of treatment ment were not different among letrozole-treated groups and after combining data, heifers treated with letrozole had higher plasma LH concentrations than saline-treated controls (P=0.01; FIG. 3).

Figure 4:
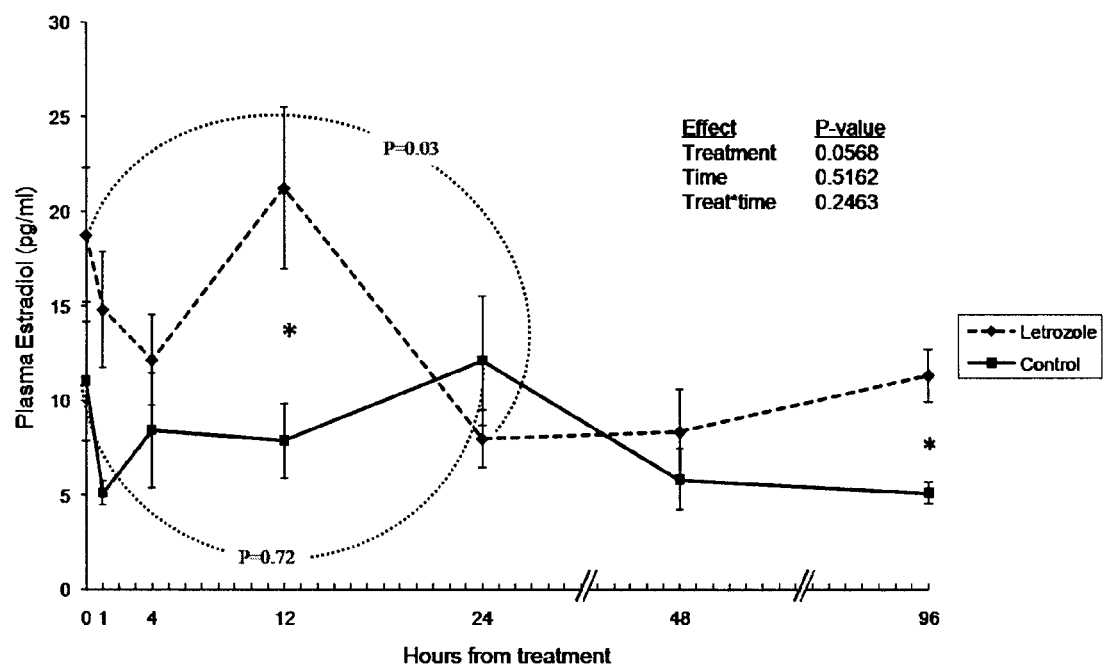
FIG. 4 is a line graph depicting plasma estradiol concentrations in heifers during the first 96 hours after a single intravenous dose of letrozole given four days after follicular ablation (plasma estradiol concentrations (mean±SEM) in heifers during the first 96 hours after a single intravenous dose of letrozole (high-, medium- and low-dose groups combined; n=29) given 4 days after follicular ablation (i.e., 2.5 days after wave emergence), compared to PBS-treated controls (n=10). Within groups, differences in estradiol concentrations between 0 and 24 hours after treatment were compared by paired t-test.*Values differed between groups (P<0.03))

Plasma estradiol concentrations did not differ among the letrozole-treated groups; hence, data were combined for comparison with saline-treated controls. Mean plasma concentrations of estradiol over the 4-day period after treatment tended to be higher in letrozole-treated heifers compared to control heifers (P=0.06), primarily as a result of an increase between 4 and 12 hours after treatment in letrozole-treated heifers (FIG. 4). Plasma estradiol concentrations decreased by nearly 50% from 0 to 24 hours after treatment in letrozole-treated heifers (from 15.2±3.01 to 8.0±1.51 pg/mL; P=0.03) while no change occurred in control heifers (from 11.0±3.16 to 12.1±3.43 pg/mL, P=0.72).

Plasma Letrozole Concentration

Figure 5:
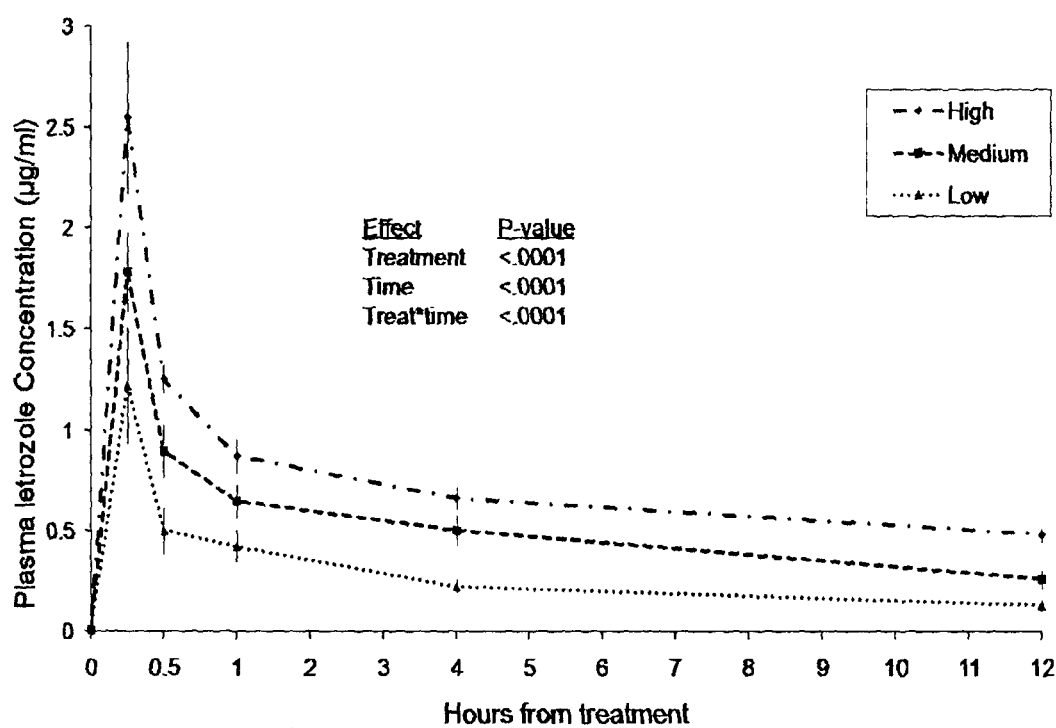
FIG. 5 is a line graph depicting plasma letrozole concentration as determined by HPLC/MS after administration of letrozole (plasma letrozole concentration (mean±SEM) as determined by HPLC/MS after administration of a single intravenous dose of 125, 250, or 500 µg/kg. Data from Hour 0 to 12 hours after treatment are depicted)

Plasma letrozole concentrations, as determined by LC/MS/MS, followed a dose-dependent pattern (FIG. 5). Mean plasma concentrations throughout the 8-day period were 0.63±0.04 µg/mL, 0.44±0.04 µg/mL, and 0.27±0.04 µg/mL for high-, medium- and low-dose groups, respectively (P<0.0001). Pharmacokinetic parameters are summarized in Table 2. No significant differences were detected among dose-groups in the half-life (T1/2), volume of distribution (Vz/f), systemic clearance (CIS) and mean residence time (MRT). Maximal concentration (Cmax) and area under the curve (AUClast) differed between high, medium and low doses following a dose-dependent pattern (P=0.007 and P<0.0001, respectively).

TABLE 2

Pharmacokinetics of letrozole after administration of a single intravenous dose of 125, 250, or 500 µg/kg in postpubertal beef heifers, determined by non-compartmental analysis (mean ± SEM).

| Parameter | 125 µg/kg (n = 9) | 250 µg/kg (n = 9) | 500 µg/kg (n = 9) | Combined |
|---|---|---|---|---|
| Maximal concentration ($C_{max}$) (µg/mL) | $1.2 \pm 0.25^a$ | $1.7 \pm 0.18^b$ | $2.5 \pm 0.37^c$ | $1.8 \pm 0.27$ |
| Half-life ($T_{1/2}$) (hours) | $26.9 \pm 0.95^a$ | $26.6 \pm 1.18^a$ | $28.5 \pm 1.05^a$ | $27.3 \pm 0.42$ |
| Area under the curve ($AUC_{last}$) (hours × µg/mL) | $8.8 \pm 0.72^a$ | $17.3 \pm 2.00^b$ | $28.1 \pm 2.15^c$ | $18.2 \pm 4.03$ |
| Volume of distribution ($V_z/f$) (mL/kg) | $566.2 \pm 43.95^a$ | $592.9 \pm 66.06^a$ | $745.7 \pm 7.35^a$ | $634.9 \pm 39.54$ |
| Systemic clearance ($Cl_s$) (mL/hour/kg) | $14.6 \pm 1.10^a$ | $15.5 \pm 1.75^a$ | $18.5 \pm 1.67^a$ | $16.2 \pm 0.83$ |
| Mean residence time (MRT) (hours) | $31.7 \pm 2.00^a$ | $33.7 \pm 2.98^a$ | $35.8 \pm 1.43^a$ | $33.7 \pm 0.84$ |

$^{abc}$Within rows, values with no common superscript are different (P < 0.05)

Circulating Hormone Concentrations

Figure 2:
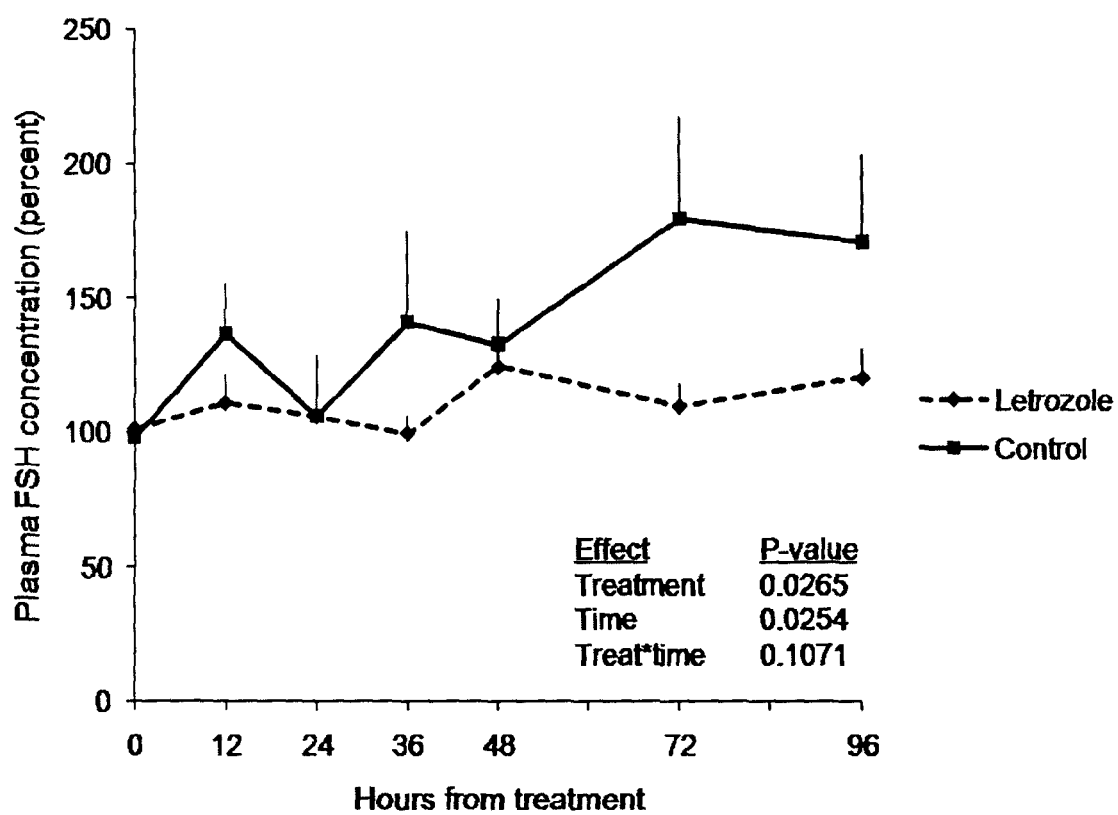
FIG. 2 is a line graph depicting plasma FSH concentrations in heifers treated with letrozole (plasma FSH concentrations (percent change after treatment; mean±SEM) in heifers treated with letrozole (high-, medium- and low-dose groups combined; n=29) 4 days after follicular ablation (i.e., 2.5 days after wave emergence), compared to saline-treated controls (n=10))

Plasma FSH concentrations during the 4 days after treatment were not different among letrozole-dose groups; hence, data were combined for comparison with saline-treated controls. Plasma FSH levels tended to increase in both letrozole and control groups, but proportionately less in the letrozole-treated animals (FIG. 2). By 72 hours after treatment, plasma FSH concentrations were lower in heifers treated with letrozole than in controls (P<0.03).

Plasma LH concentrations during the 12-hour period after treatment did not differ among letrozole-treated groups; hence, data were combined for comparison with PBS-treated controls. Heifers treated with letrozole had higher plasma LH concentrations than saline-treated controls during the first 12 hours following treatment (P=0.05; FIG. 3). Similarly, plasma LH concentrations during the 4-day period after treat- Discussion—I As shown herein, a single treatment with letrozole on Day 3 post-ovulation in cattle, regardless of the dose, significantly lengthened the period of dominance of the extant dominant follicle, resulting in a prolonged interval to emergence of a new follicular wave. Furthermore, the mean diameter achieved by the dominant follicle was significantly larger in letrozole-treated heifers. Letrozole treatment was associated with elevated plasma LH concentrations, but had no apparent effect on FSH concentrations.

Mean plasma estradiol concentrations in letrozole-treated heifers tended to be higher than in controls for the first 4 days after treatment, but this was attributed primarily to a significant and sharp elevation at 12 hours after letrozole treatment. This acute elevation in estradiol has not been reported in women, but a similar increase was observed in rats, and was interpreted as the result of a gonadotrophin release caused by letrozole treatment [54]. Although in the present study plasma estradiol concentrations decreased by nearly 50% by 24 hours after letrozole treatment, concentrations were not significantly lower than controls.

The lack of an apparent suppressive effect of letrozole on estrogen concentrations in cattle in the present study may have been the result of insufficient assay sensitivity and/or an inadequate dose of letrozole. In women, basal and maximum circulating estradiol concentrations have been reported to be approximately 20 and 200 pg/mL, respectively [55]. In the heifers examined in this study, basal plasma estradiol concentrations were below the detection limit (3 to 4 pg/mL) and, on average, maximum concentrations did not exceed 25 pg/mL during the first 8 days after ovulation. In addition, the dose and duration of letrozole treatment used in our experiment may not have been sufficient to inhibit estradiol production in cattle, in contrast to other species in which treatment resulted in a marked reduction in circulating estradiol concentrations (97-99% in post-menopausal women [30], and 88% in boars [56]).

Extended growth and delayed regression of the extant dominant follicle was attributed to letrozole-induced elevation in plasma LH concentrations. Endogenous concentrations of LH began to rise 2 hours after letrozole was administered and levels were elevated for at least 4 days after treatment. Increasing concentrations of LH during this time may also have elicited the surge in plasma estradiol concentrations observed 12 hours post-treatment.

Plasma FSH concentrations were lower in letrozole-treated heifers than in controls. While not wishing to be bound by theory, follicular products other than estradiol also suppress FSH and may be responsible for the effect observed [8, 57, 58]. Inhibin is secreted by the dominant and subordinate follicles during the time of follicular deviation and, together with estradiol, has been associated with the suppressive effects involved in follicular selection and dominance [59, 60]. However, letrozole treatment in the present study was associated with over-dominance (prolonged growth and maintenance of the dominant follicle) resulting in an extended period of FSH suppression and delayed emergence of the next follicular wave. Inhibition of estradiol synthesis by an aromatase inhibitor did not adversely affect the extant dominant follicle, rather it indirectly enhanced follicular dominance by permitting elevated pituitary LH secretion.

Although most of the studies in women in which letrozole was used to treat unexplained infertility are based on a 5-day treatment regimen (total dose of 12.5 to 20 mg letrozole), single dose treatments of 20 mg administered orally on the third day of the menstrual cycle have been reported to be equally effective in suppressing circulating estrogen concentrations. The half-life of letrozole in humans has been reported to be approximately 2 days which could result in effective suppression of estradiol production for 4 to 6 days after a single administration [46]. From the pharmacokinetic parameters reported in the present study it is estimated the half-life of letrozole in heifers to be 27 hours (as apposed to 48 hours in women [41, 61]), the mean residence time (average duration of persistence in the body) to be 34 hours (as apposed to 59 hour in women [41]), and the volume of distribution to be 635 mL/kg (as apposed to 1870 mL/kg in women [41]). Taken together, these data are interpreted to suggest that cattle may require a higher dose and a longer period of exposure to achieve effective concentrations in target tissues.

In summary, letrozole treatment in heifers was associated with elevated circulating LH concentrations and an extended period of dominance of the dominant follicle present at the time of treatment, regardless of dose. Consequently, circulating concentrations of FSH remained suppressed and emergence of the next wave was delayed.

Example—II

Material and Methods—II

Cattle

Hereford-cross beef heifers, 14 to 20 months of age and weighing between 233 and 404 kg, were chosen from a herd of 50 animals maintained in outdoor corrals at the University of Saskatchewan Goodale Research Farm (52° North and 106° West). Heifers were fed alfalfa/grass hay and grain to gain approximately 1.3 kg per day and had water ad libitum during the experimental period from May to July. Heifers were initially examined by transrectal ultrasonography (7.5 MHz linear-array transducer, Aloka SSD-900; Tokyo, Japan) to confirm that they were postpubertal by the presence of a CL [33].

Treatments and Examinations

Heifers in which a CL was detected during the initial examination underwent transvaginal ultrasound-guided follicular ablation of the two largest ovarian follicles to synchronize follicular wave emergence, which was expected to occur 1 to 1.5 days later [34, 35]. Four days after follicular ablation, heifers were given 500 µg of cloprostenol (PGF, Estrumate, Schering-Plough Animal Health, Pointe-Claire, QC, Canada) intramuscularly (im) to induce regression of the CL and to synchronize ovulation [36]. The experiment was performed in two replicates (n=20-27 per replicate) and each heifer was used only once. In replicate 1, heifers were assigned randomly at the time of ovulation (Day 0) to the following groups and given a 3-day regimen of letrozole from Days 1 to 3 (n=5), Days 3 to 5 (n=5), Days 5 to 7 (n=5), or no treatment (control group, n=5). In replicate 2, heifers were similarly assigned to groups and given letrozole from Days 1 to 3, (n=5), Days 3 to 5 (n=4), or Days 5 to 7 (n=4), but untreated control heifers were arranged in three sub-groups to serve as contemporaneous controls for each letrozole-group during intensive blood sampling periods (i.e., control Days 1 to 3, n=4; control Days 3 to 5, n=4; and control Days 5 to 7, n=5). For practical purposes, the total dose of letrozole (250 µg/kg) was calculated on the basis of an average weight of 350 kg for all heifers and administered intravenously in daily divided doses over 3 days (85 µg/kg per day). For intravenous injection, letrozole was prepared in 95% ethanol to a final concentration of 5 mg/ml, resulting in an injection volume of 6 mL/day.

Ovarian Ultrasonography

Ultrasound examinations were recorded on a sketch sheet in which each ovary and its structures (CL [37] and follicles ≥4 mm in diameter [38]) were represented in size and relative location. Ovulation was defined as the disappearance of any follicle ≥8 mm between two consecutive daily examinations, and was confirmed by the subsequent development of a CL [39]. Follicular wave emergence was defined retrospectively as the day when the dominant follicle was first identified at a diameter of 4 or 5 mm [40, 41]. If the dominant follicle was not identified until it reached 6 or 7 mm, the previous day was considered the day of follicular wave emergence [42]. The dominant follicle of a wave was defined as the largest antral follicle of that wave after deviation, and the first subordinate follicle as the second largest antral follicle originated from the same wave [43]. The day of onset of follicular and luteal regression was defined as the first day of an apparent constant decrease in follicular and luteal diameters, respectively [40].

Ultrasound Image Analysis

Ultrasound images from a subset of letrozole-treated (n=4-5 per group) and control (n=6) heifers were recorded throughout the duration of treatment for computer-assisted image analysis. Images were analyzed using a series of custom-developed computer algorithms optimized for ultrasonography (SYNERGYNE Version 2.8© Saskatoon, Saskatchewan) on a Sun Sparc Station (Sun Microsystems, MT View, Calif.) computer [44-46]. Echotexture was defined in terms of mean pixel value and pixel heterogeneity. Mean pixel values were quantified using a grey-scale ranging from 0 (black) to 255 (white). The pixel heterogeneity was the standard deviation of grey-scale values of all the pixels within the user-defined region of measurement. Spot analysis of the follicular antrum and corpus luteum, and line analysis of the peripheral antrum, follicular wall and stroma were done as previously described [47]. For spot analyses, the follicular antrum and the CL wall were divided into four quadrants and the sampling area encompassed 75 to 80% of each quadrant. For line analyses, a straight line was drawn transversing the follicular wall from peripheral antrum to stroma and the pixel values along that line were measured in areas located within the 10 and 2 o'clock position of the follicles [45].

Collection of Blood Samples

Blood samples were collected by jugular or coccygeal venipuncture into 10 ml heparinised, vacuum tubes (Vacutainer tubes; Becton Dickinson Vacutainer Systems, Franklin Lakes, N.J., USA). Blood samples were collected daily from pre-treatment ovulation to post-treatment ovulation. In replicate 1, additional samples were collected from letrozole-treated heifers every 12 hours from the beginning of treatment to first wave emergence. In replicate 2, heifers were sampled at 15 minute intervals for the first 8 hours after the second dose of letrozole (i.e., second day of treatment) using an indwelling jugular catheter, as described previously [48]. Blood samples were centrifuged at 1500×g for 20 minutes, and plasma was separated and stored in plastic tubes at −20° C.

Hormone Assays

Plasma LH concentrations were determined in duplicate using a double-antibody radioimmunoassay (NIDDK-bLH4) [5, 49]. The minimum and maximum values along the standard curve were 0.06 and 8 ng/mL, respectively. The intra- and inter-assay coefficients of variation were 7.9% and 2.5%, respectively, for low reference samples (mean, 0.85 ng/mL) and 8.6% and 9.5%, respectively, for high reference samples (mean, 2.5 ng/mL).

Plasma FSH concentrations were determined in duplicate using a double-antibody radioimmunoassay using NIDDK-anti-oFSH-1 primary antibody and expressed as USDA bovine FSH-I1 units [5, 49]. The minimum and maximum values along the standard curve were 0.12 and 16 ng/mL, respectively. The intra- and inter-assay coefficients of variation were 11.1% and 11.2%, respectively, for low reference samples (mean, 1.9 ng/mL) and 5.2% and 4.1%, respectively, for high reference samples (mean 4.0 ng/mL).

Plasma estradiol concentrations were determined in duplicate by enzyme-linked immunosorbent assay (Cayman Chemical Company, Ann Arbor, Mich., USA). In this competitive ELISA, plasma steroid competes with acetylcholinesterase labelled steroid for the binding site on the polyclonal rabbit anti-steroid antibody. The antiserum to estradiol was reported to cross-react with estradiol-3-glucoronide (14%), estrone (12%), and estriol (0.3%). For all other steroids cross-reactivities were reported as <0.1%. The minimum and maximum values along the standard curve were 6.6 and 4000 pg/well, respectively. The intra- and inter-assay coefficients of variation for reference samples assayed in duplicate were 11.7% and 12.7, respectively. A concentration procedure using diethyl ether extraction was performed prior to the assay in all samples to increase estrogen concentration to measurable levels (ask Susan Cook for a reference for the extraction method). To confirm the effectiveness of the ELISA in quantifying estradiol concentrations in plasma, a random sub-set of plasma samples (n=25) was also analyzed by liquid chromatography tandem mass spectrometry (LCMS/MS) and results were compared to those obtained by ELISA (Appendix 1).

Plasma progesterone concentrations were determined in duplicate using a commercial solid-phase kit (Coat-A-Count; Diagnostic Products Corporation, Los Angeles, Calif., USA). The range of the standard curve was 0.1 to 40.0 ng/mL. The intra- and inter-assay coefficients of variation for samples assayed in duplicates were 10.1% and 15%, respectively, for low reference samples (mean, 1.8 ng/mL) and 5.5% and 7.7%, respectively, for high reference samples (mean, 17.5 ng/mL).

Plasma Letrozole Concentration

Plasma concentrations of letrozole were determined from samples collected every 12 hours from pre-treatment to one day after cessation of treatment using high performance liquid chromatographytandem mass spectrometry (HPLC/MS) as described in Chapter 4, Section 4.3.6.

Statistical Analyses

Statistical analyses were done using the Statistical Analysis System software package (SAS Learning Edition 9.1, 2006; SAS Institute Inc., Cary, N.C., USA). Time-series hormone data, plasma letrozole concentration, and follicular and luteal diameter profiles were analysed by repeated measures, using the PROC MIXED procedure. The main effects were treatment, time, and their interactions. Initial inspection of LH data revealed an apparent difference between morning and afternoon values, so LH data were examined by analysis of variance for repeated measures to determine the main effects of treatment (During and After), stage of follicular development (Days 1 to 3, Days 3 to 5, and Days 5 to 7), time of the day (AM vs PM), and day of treatment (1st, 2nd, and 3rd dose). Single point measurements (interwave and interovulatory intervals, interval from ovulation to onset of CL regression, mean and basal LH concentrations, LH pulse amplitude and frequency, and pharmacokinetic parameters for letrozole) were analysed by analysis of variance. Paired t-test was used to compare pixel values and pixel heterogeneity for the dominant follicles and CL using mean values of two pre-treatment images taken 24 hours and immediately before treatment and mean values of two post-treatment images taken 24 and 48 hours after the end of treatment. If no differences were detected among letrozole-treated groups, data were combined and re-analysed as a single letrozole treatment group for comparison with non-treated controls. If significant main effects or interactions ($P \leq 0.05$) were detected, Tukey's post-hoc test was used for multiple comparisons.

Due to individual variability in circulating hormone concentrations among heifers, and because our objective was to determine the effect of treatment within individuals, data on LH and FSH concentrations were transformed to a percentage of the mean concentration of the two first data points collected (Days 0 and 1) for each individual heifer before analysis of variance for repeated measures. For the same reasons, estradiol concentrations were transformed to a percentage of the mean concentration of two pre-treatment data points (i.e. for each individual heifer before statistical analysis.

For analysis of LH pulsatility, a pulse was defined as the presence of two consecutive samples (taken at 15 minute intervals) which were greater than the mean of the two previous samples (basal value) and one or both exceeding the mean basal value by more than twice the coefficient of variation of the assay [50]. The basal concentration of LH for individual heifers was defined as the mean of all the concentrations excluding those that were included in the definition of a pulse. Pulse amplitude was determined by the difference between LH pulse height (the highest concentration of LH within a pulse) and the basal concentration [51]. All values are expressed as mean±SEM.

Animal procedures were performed in accordance with the Canadian Council on Animal Care and were approved by University of Saskatchewan Protocol Review Committee.

Results—II

Circulating Concentrations of Letrozole

Figure 6:
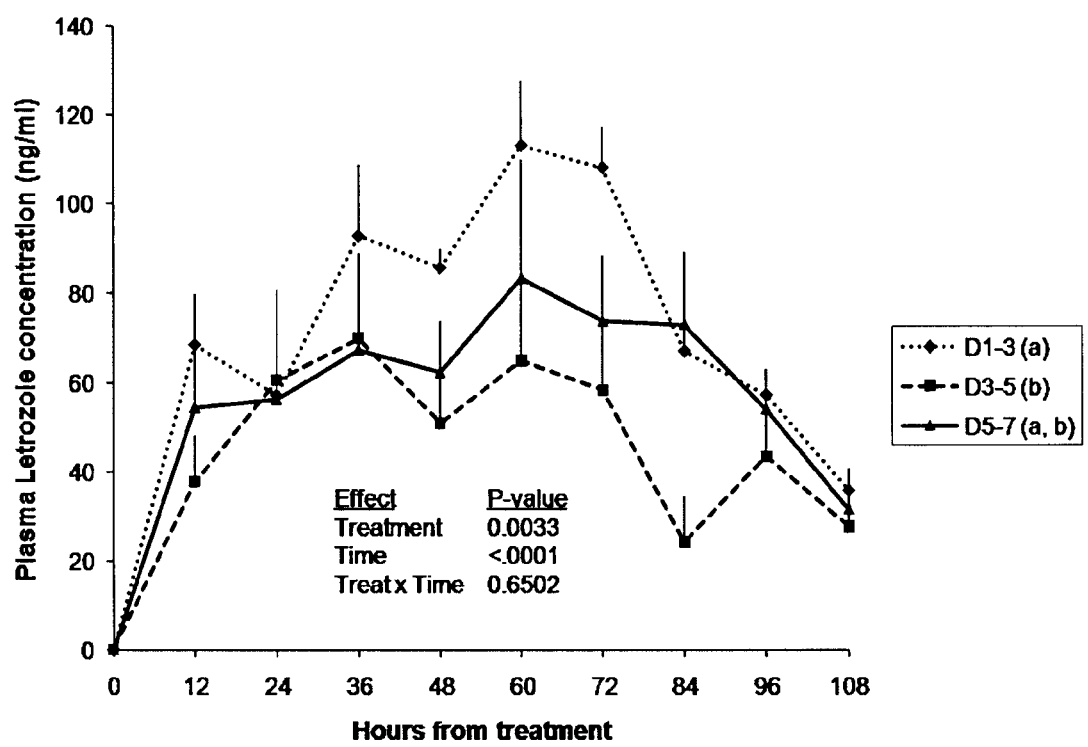
FIG. 6 is a line graph depicting plasma letrozole concentrations in heifers treated with letrozole (plasma letrozole concentration (mean±SEM) in heifers treated with letrozole (85 µg/kg/day) from Days 1 to 3, Days 3 to 5 or Days 5 to 7

Plasma letrozole concentrations in all three treatment groups were elevated by 12 hours after initiation of treatment and reached peak levels by 60 hours, followed by a decline to approximately half peak values by 108 hours (time effect, $P<0.001$; FIG. 6). Heifers treated from Days 1 to 3 had higher circulating letrozole concentrations than those treated from Days 3 to 5, while those treated from Days 5 to 7 were intermediate (overall means, 68.6±4.79, 43.9±4.75 and 55.6±4.75 ng/ml, respectively, $P<0.01$; FIG. 6).

Ovarian Follicles and Estradiol

The diameter profile of the extant dominant follicle (i.e., the dominant follicle present at the time of treatment) was similar among letrozole treatment groups; hence, data were combined for comparison with controls. The dominant follicle grew longer and to a greater diameter in letrozole-treated heifers than in controls ($P<0.01$; FIG. 7). The dominant follicle regressed later, and the inter-wave interval was longer in letrozole-treated heifers than in controls. ($P<0.05$; Table 3). However, the inter-ovulatory interval did not differ between groups.

Plasma estradiol concentrations for each treatment group were compared independently with the respective control subgroup for each treatment period (FIG. 9). Estradiol concentrations were not different between letrozole-treated and control heifers, regardless of the stage of follicular development at the time of treatment (FIG. 9).

Corpus Luteum and Plasma Progesterone

Figure 10:
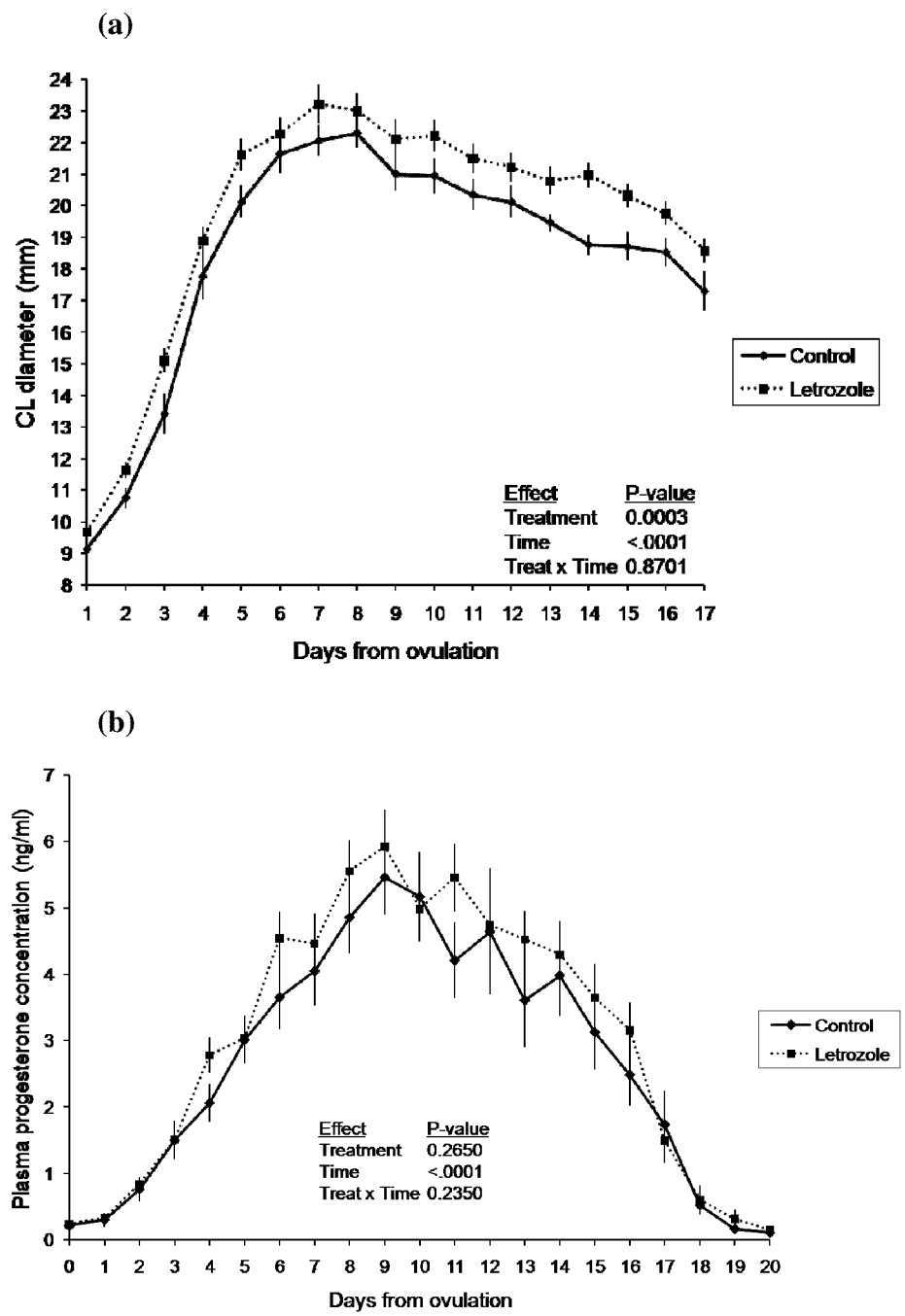

No differences in CL diameter were detected among letrozole-treated groups; hence, data for the three treatment groups were combined for comparison with untreated controls. The day-to-day CL diameter profile of heifers treated with letrozole was larger than that of controls ($P<0.004$; FIG. 10). Plasma progesterone concentrations did not differ among treatment groups, and data were combined for comparison with controls (FIG. 10). Though numerically higher throughout the sampling period in the letrozole-treated group than in the control group, differences in plasma progesterone concentrations were not significant (FIG. 10).

Computer-Assisted Ultrasound Image Analysis

Spot analysis of the CL: Mean pixel values and pixel heterogeneity of images of the CL were not affected by letrozole treatment compared to controls. No significant changes in mean pixel values or in heterogeneity were detected between pre- and post-treatment periods (FIG. 15).

Spot analysis of the dominant follicle antrum: Although post-treatment values were consistently lower than pre-treatment values in all letrozole-treated groups, mean pixel values and heterogeneity were not affected significantly by treatment during any of the three periods of the first follicular wave, nor was there a significant interaction of treatment and time (FIG. 15)

Line analysis of the dominant follicle wall: Mean pixel values recorded in heifers treated with letrozole from Days 1 to 3 after ovulation increased ($P<0.06$) between pre- and post-treatment evaluation while it remained unchanged in control heifers. However, significantly lower pre-treatment samples were observed in the letrozole-treated group and that might account for the difference observed between controls and heifers treated from Days 1 to 3. There was no effect of letrozole on pre- and post-treatment mean pixel values or

TABLE 3

Effects (mean ± SEM) of a 3-day regimen of letrozole given at three different stages of the follicular wave in heifers on the intervals to new wave emergence and ovulation.

|  | Letrozole treatment | | | |
| --- | --- | --- | --- | --- |
|  | Days 1 to 3 (n = 10) | Days 3 to 5 (n = 9) | Days 5 to 7 (n = 9) | Control (n = 17) |
| Inter-wave interval (days) | 8.9 ± 0.35$^a$ | 10.0 ± 0.37$^{ab}$ | 10.7 ± 0.37$^b$ | 7.6 ± 0.27$^c$ |
| Inter-ovulatory interval (days) | 20.9 ± 0.46$^a$ | 20.1 ± 0.49$^a$ | 21.2 ± 0.49$^a$ | 20.5 ± 0.35$^a$ |
| Dominant follicle diameter at treatment (mm)* | 6.8 ± 0.36$^a$ | 10.1 ± 0.45$^{bc}$ | 12.1 ± 0.43$^d$ | 6.5 ± 0.27 (Day 1)$^a$<br>9.4 ± 0.32 (Day 3)$^b$<br>11.2 ± 0.30 (Day 5)$^{cd}$ |

$^{abcd}$Within rows, values with no common superscript are different (P < 0.05).
*Compared to respective controls at the same stage of follicular development.

The diameter profile of the largest subordinate follicle in heifers treated with letrozole from Days 1 to 3 was larger than that of control heifers ($P<0.05$; FIG. 8). The diameter profiles of the largest subordinate follicle in heifers treated with letrozole from Days 3 to 5 and Days 5 to 7 were intermediate and did not differ from either of the other two groups.

heterogeneity along the follicular wall heifers treated on Days 3 and 5, and Days 5 and 7, compared to controls (FIG. 15).

Gonadotropins

No differences were detected in plasma FSH levels between letrozole-treated heifers compared with their respective controls (FIG. 11).

No significant differences in plasma LH concentrations were detected among groups using daily samples. To examine the effects on LH more critically, additional 12-hour samples (i.e., PM samples), originally taken in letrozole-treated heifers for measurement of letrozole, were also analyzed. Since PM samples were not obtained from control animals, the control group was not included in the analysis. Plasma LH concentrations were analyzed to determine the effect of time of sampling (AM vs PM), day (1st, 2nd, and 3rd), period (3 days of treatment vs 3 days after treatment), and the follicular stage when treatment was initiated (Days 1 to 3, Days 3 to 5, or Days 5 to 7). The overall model revealed no significant effect or interaction involving follicular stage; hence, the effect of follicular stage was removed from the model before further analysis (FIG. 12). Interactions between day (1st, 2nd, 3rd) and time (AM vs PM), and between treatment period (during vs after treatment) and time (AM vs PM) were significant. All PM samples collected during treatment were significantly higher (188.5128.50%) than AM samples collected during treatment (93.6±14.85%) and AM and PM samples collected after cessation of treatment (79.3114.64 and 78.9127.91%, respectively; FIG. 13).

Plasma LH values determined in samples taken at 15 minute intervals for 8 hours after the second dose of letrozole were compared to their respective controls to determine the effect of treatment on mean and basal concentrations, pulse amplitude, and pulse frequency for each treatment interval (Table 4). No differences between letrozole vs controls groups were found for any of the parameters analyzed in any of the treatment periods.

TABLE 4

Effect of 3-day letrozole treatment at three different stages of the follicular wave on LH secretory activity compared to corresponding controls as measured in 15 min samples collected over 8 hours.

| Treatment period | Group | Mean LH (ng/mL) | Basal LH (ng/mL) | LH pulse amplitude (ng/mL) | LH pulse frequency (pulses/h) |
|---|---|---|---|---|---|
| Day 1-3 | control | 0.58 ± 0.12 | 0.41 ± 0.09 | 0.65 ± 0.20 | 0.92 ± 0.04 |
|  | treated | 0.52 ± 0.15 | 0.38 ± 0.11 | 0.46 ± 0.15 | 0.95 ± 0.08 |
| Day 3-5 | control | 0.15 ± 0.03 | 0.1 ± 0.03 | 0.21 ± 0.04 | 0.66 ± 0.08 |
|  | treated | 0.15 ± 0.5 | 0.08 ± 0.03 | 0.40 ± 0.18 | 0.53 ± 0.03 |
| Day 5-7 | control | 0.15 ± 0.06 | 0.09 ± 0.03 | 0.45 ± 0.11 | 0.41 ± 0.06 |
|  | treated | 0.21 ± 0.04 | 0.13 ± 0.02 | 0.88 ± 0.37 | 0.41 ± 0.08 |

Discussion—II

As shown in Example II, a 3-day letrozole treatment of post-pubertal beef heifers at different stages of development of the dominant follicle of the first follicular wave did not consistently decrease circulating estradiol concentrations, nor did induce a surge in FSH or hasten emergence of a new follicular wave. On the contrary, letrozole treatment caused the extant dominant follicle to continue growth, prolonging its period of dominance and extending the interval to emergence of the next follicular wave. In women, treatment with letrozole from Days 3 to 7 after the beginning of menses has been reported to cause emergence of a new wave of follicular development shortly after the initiation of treatment [28]. While not wishing to be bound by theory, the mechanism responsible for this effect was hypothesized to involve removal of the negative feedback effect of estradiol on pituitary FSH secretion resulting in an endogenous surge in plasma FSH which recruits a new cohort of growing follicles. The reason(s) for these differences between species are not immediately clear.

The dominant follicle diameter profiles reported herein document that 85 µg/kg/day of letrozole given intravenously in a 3-day regimen (250 µg/kg total) did not terminate dominant follicle growth, regardless of whether treatment was initiated before, during or after selection of the dominant follicle. A single intravenous dose of 250 µg/kg of letrozole given to post-pubertal heifers on Day 3 (day of dominant follicle selection) had a similar effect: significant lengthening of the period of dominance of the extant dominant follicle and a prolonged interwave interval (Example I). Continued growth of the dominant follicle, as well as the CL, was attributed to increased circulating concentrations of LH in letrozole-treated heifers. Results from computerized image analysis supported the notion that dominant follicle viability was not modified by letrozole treatment during any of the treatment stages assessed in the present study.

Another unexpected finding was the continued growth of the largest subordinate follicle in heifers treated with letrozole from Day 1 to 3 after ovulation; it grew larger and for longer period of time compared to controls. As plasma LH concentrations were higher by 12 hours after the first administration of letrozole, perhaps elevated LH was responsible for continued growth of subordinate follicles during treatment on Days 1 to 3. Growing follicles within a follicular wave are FSH-dependent to approximately 3 days after wave emergence when LH receptors begin to express, leading to a shift in gonadotrophin responsiveness [40, 41, 53-55]. As this shift to LH responsiveness is not an all-or-nothing phenomenon as subordinate follicles are capable of assuming dominance [Adams et al., 1993], while not wishing to be bound by theory, it is plausible that growing subordinate follicles become responsive to LH before selection is complete (e.g., Day 2 of the follicular wave) and that elevated LH concentrations induced by letrozole treatment were stimulatory to the growth of the largest subordinate follicle. However, as the number and responsiveness of LH receptors in such follicles are likely to be far lower than that of the future dominant follicle [56, 57], and due to decreasing LH concentrations once treatment with letrozole was interrupted; such subordinate follicles could not maintain their growth, and eventually underwent atresia.

Plasma LH concentrations were modified by the 3-day letrozole treatment in a particular fashion. A cycle-like pattern was observed in the three letrozole-treated groups; an elevation of LH concentrations occurred by 12 hours after letrozole treatment followed by a decline to baseline within 24 hours. This could partially explain the lack of significant differences between the different treatment groups and their respective controls when only daily data (collected AM) were analyzed. Although the understanding of ultradian or circadian variations on LH secretion in cattle and other mammals is contradictory, with some authors reporting higher diurnal levels [58, 59] and other favoring the presence of higher nocturnal levels [60]; the fact that evening increases in circulating LH concentrations were only found during the period of treatment, and were not seen once treatment was interrupted, tends to rule out the possibility of a diurnal-nocturnal variation as a responsible for such increases. Furthermore, diurnal and nocturnal variations have been reported to range between 25 to 50% [58, 60], while in our results the evening values during treatment doubled the morning values during and after treatment. The reasons for the lack of effect of letrozole treatment on LH pulse frequency, amplitude, and LH mean and basal mean values for samples collected every 15 min for the for 8 hours after treatment [62] are not clear.

The effect of letrozole treatment on mean plasma estradiol response was inconsistent among the three treatment periods assessed in this experiment. Although not significant, it appeared that the group of heifers receiving letrozole from Days 5 to 7 after ovulation had higher plasma estradiol concentrations compared to controls. The reason(s) for this difference is not immediately clear. While not wishing to be bound by theory, it could be possible that differences are related to the stage of development of the extant dominant follicle. The third treatment period encompassed the early/late static phase of the dominant follicle, a time when estrogen synthesis might be expected to start declining. In controls heifers, in which next wave emergence occurred in average around Day 7.6 after ovulation, decreasing circulating levels of estradiol were already observed by Day 5. However, in heifers treated with letrozole from Day 5 to 7 post-ovulation, the dominant follicle stayed viable and producing estradiol for longer; thus, wave emergence did not happen, in average, until Day 10.7 post-ovulation.

Unexpectedly, mean letrozole concentration was lower in heifers treated from Days 3 to 5 than those treated form Days 1 to 3, although this observation is more likely due to differences in real body weight among heifers within each treatment group rather than an effect of the stage of follicular development. The mean concentrations of letrozole in the circulation 96 hours after 250 µg/kg were divided in a 3-day regimen or given in a single dose were similar (51.6±4.33 ng/mL vs 43.7±8.79 ng/mL, respectively). However, during those first 96 hours, the mean circulating levels of letrozole after the 3-day protocol were lower compared to those of heifers given the same dose in a single application (60.8±3.36 vs 112±16.26 ng/ml). It could be speculated that the single injection of letrozole at a dose of 250 µg/kg was marginal in suppressing estradiol production, while splitting this dose into three daily injections resulted in sub-thresh-hold doses that inconsistently inhibited of estradiol production in this study.

In summary, 250 µg/kg of letrozole, given in a 3-day regimen, elevated LH secretion resulting in larger dominant follicle and CL profiles and prolonged interwave intervals, regardless the stage of follicular development during which treatment was applied. Follicle-stimulating hormone levels in plasma were not affected by letrozole administration during any of the treatment periods in this trial. While not wishing to be bound by theory, it is speculated that the inconsistent and minimal inhibition of estradiol production accounts for the lack of effect on FSH secretion. Based on the circulating concentrations of letrozole achieved in this study, it could be concluded that a total dose of 250 µg/kg of letrozole divided into three doses of 85 µg/kg is insufficient to consistently inhibit aromatase activity and estradiol secretion. With these sub-threshold treatment doses of letrozole, individual animal sensitivity to aromatase inhibition could play an important role in the variation observed in the present study. However, the results continue to support that higher levels of letrozole may be needed to achieve a consistent and durable inhibition of estradiol production necessary to predictably affect gonadotrophin secretion and follicular dynamics in cattle.

Example—III

Material and Methods—III

Ovarian cyclicity in heifers was synchronized using transvaginal ultrasound-guided follicular ablation followed by a double dose of PGF 4 days after ablation. The ovaries were examined daily by transrectal ultrasonography to detect ovulation. Three days after ovulation, heifers were assigned randomly to four treatment groups and given letrozole at a dose of 1 mg/kg intravenously (in benzyl alcohol, n=10) or intramuscularly (in benzyl alcohol plus canola oil 1:1 v/v, n=10), or given a placebo intravenously (benzyl alcohol, n=5) or intramuscularly (benzyl alcohol plus canola oil 1:1 v/v, n=5). Ovarian structures were monitored by ultrasonography and blood samples were collected by jugular venipuncture twice daily from pre-treatment to post-treatment ovulations. Comparisons among groups were made by one-way ANOVA for single-point measurements and by ANOVA for repeated measures for time-series data.

Blood samples collected daily from treatment to post-treatment ovulation.

Sub-set of heifers bled frequently: at catheter placement and at 0, 0.25, 0.5, 1, 1.5, 2, 3, 4, 6, 8, 12, 24, 36, 48 h after treatment Transrectal ultrasonography: daily from PGF treatment to the first ovulation post-treatment.

Endpoints are: Follicular diameter profiles; CL diameter profile; Circulating progesterone concentration; Circulating FSH and LH profiles; Letrozole profile and bioavailability; Circulating estradiol concentration Follicular fluid estradiol concentration).

Results—III

Figure 17:
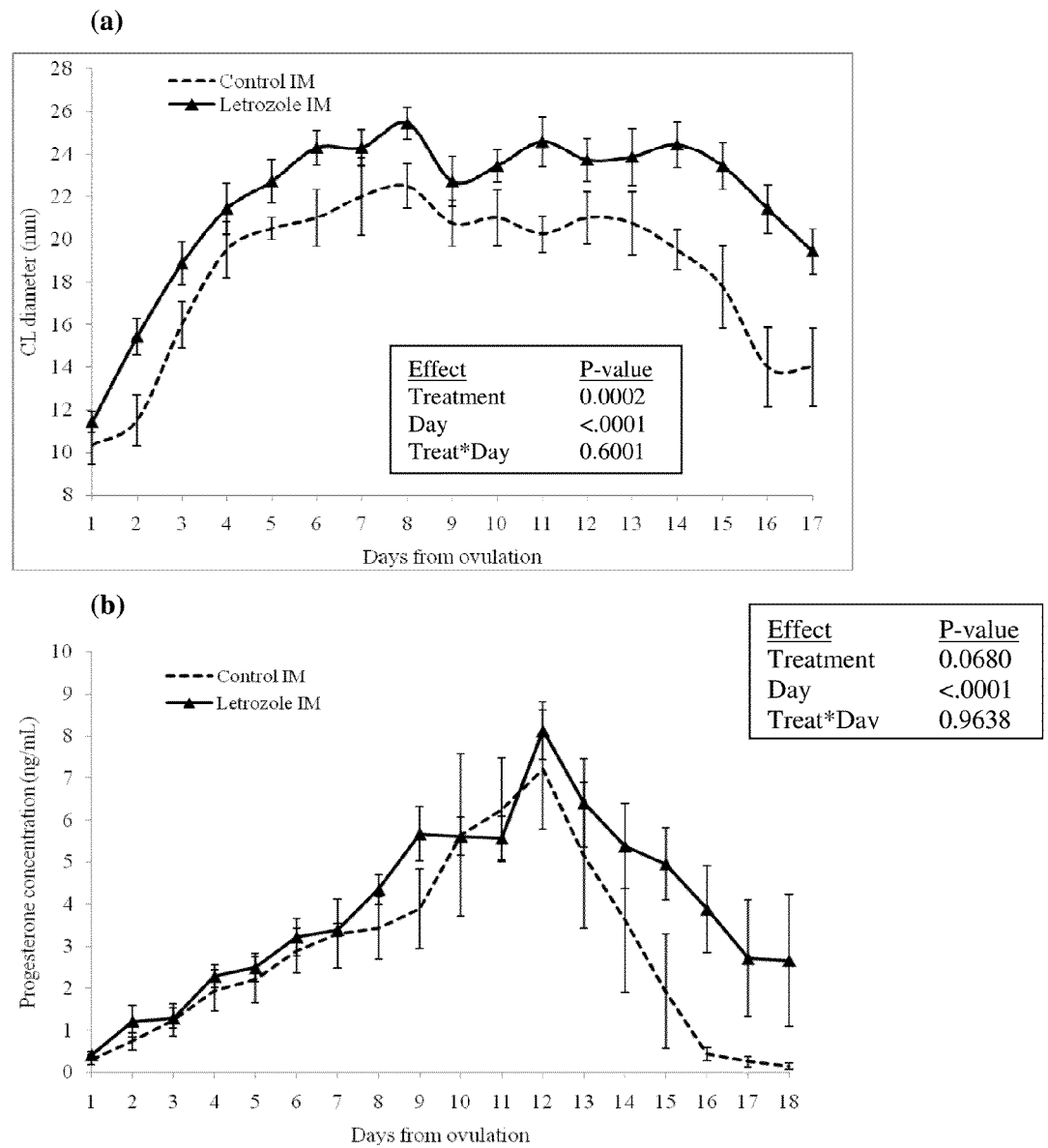

The day-to-day diameter profile of the dominant follicle was not different among groups (FIG. 16). The inter-wave interval was longer (P<0.05) in heifers treated with letrozole intramuscularly (11.7 days) than in controls (10 and 9.5 days for intravenous and intramuscular controls, respectively); the interval in heifers given letrozole intravenously was intermediate (10.6 days) and did not differ from the other groups. No significant difference was detected in interovulatory interval among groups. The day-to-day diameter profile of the corpus luteum was larger (P<0.05) and plasma progesterone concentrations tended to be higher (P<0.06) in heifers treated with letrozole intramuscularly than in controls treated intramuscularly (FIG. 17). Plasma LH concentrations did not differ among groups.

|  | Control IM | Letrozole IM | Control IV | Letrozole IV |
|---|---|---|---|---|
| Interwave Interval (Days ± SEM) | 9.5 ± 0.50$^a$ | 11.7 ± 0.34$^b$ | 10.0 ± 0.43$^a$ | 10.6 ± 0.30$^{a,b}$ |
| Interovulatory Interval (Days ± SEM) | 18.2 ± 1.10 | 19.7 ± 0.83 | 17.5 ± 1.10 | 18.9 ± 0.70 |
| DF Diameter at Treatment (mm ± SEM) | 11.0 ± 0.86 | 10.2 ± 0.61 | 11.2 ± 0.86 | 10.9 ± 0.61 |

$^{a,b}$Within rows values with no common superscript are different (P < 0.05)

Discussion—III

Letrozole dissolved in benzyl alcohol and given intravenously at a dose of 1 g/kg did not alter ovarian function in cattle, but the same dose given intramuscularly in canola oil vehicle resulted in a longer inter-wave interval, a greater CL diameter profile, and higher plasma progesterone concentrations compared to controls.

Letrozole dissolved in benzyl alcohol and canola oil and given intramuscularly resulted in a longer inter-wave interval, a greater CL diameter profile, and greater plasma progesterone concentration. The same dose given intravenously it did not seem to alter gonadotropin secretion or ovarian function. Intramuscular administration of letrozole in oil is a feasible route for the development of an aromatase inhibitor-based treatment for herd synchronization in cattle.

Example IV

To test the hypothesis that letrozole treatment during the preovulatory stage, initiated prior to onset of follicular selection and prolonged for a 7-day period will be able to induce the development of more than one follicle to a preovulatory size and to delay the occurrence of ovulation. To develop a practical route of administration of letrozole in cattle.

Materials and Methods—IV

Five to eight days after PGF-induced ovulation, FA was performed followed by a double dose of PGF 60 and 72 hr later. Heifers were randomly divided into two groups and received from Day 1 (Day 0=wave emergence) until Day 7 or until ovulation is detected:
intravaginal device containing 1 g of letrozole (n=15)
Intravaginal blank device (letrozole free, n=15)
Transrectal ultrasound examination and blood sample collection were performed daily from day of ablation until Day 12 post-ovulation. blood samples were collected frequently at the time of catheter placement, at 0, 10, 20, 30 min, 1, 1.5, 2, 3, 4, 6, 8, 12 and 24 hours post-treatment Discussion—IV A prolonged treatment with letrozole delayed ovulation for 24 hours. Induced the ovulation of a larger DF. Did not induced larger CL, however the CL produced higher levels of progesterone. Potential to improve post-AI fertility in dairy cows and post-transfer fertility in recipients. An intravaginal device in a feasible route of administration of letrozole for the development of synchronization protocols
Protocols
Use of Letrozole to Control Ovarian Dynamics in Cattle As noted above, letrozole has the capability to lengthen the lifespan and period of dominance of the extant dominant follicle in the ovaries of cattle. A luteotrophic effect of letrozole in cattle as also been shown. Letrozole may be used to control ovarian dynamics in cattle in respect of (i) herd synchronization, (ii) improved fertility and (iii) twinning.
Herd Synchronization In one example, a slow-release device containing letrozole may be applied on random days of the estrous cycle to induce the formation of a persistent dominant follicle and delay wave emergence by preventing spontaneous ovulations (i.e., inhibiting the pre-ovulatory rise in estradiol and potentially delaying luteolysis). On Day 5 (Day 0=day of treatment), a luteolytic dose of PGF is given to induce regression of the corpus luteum (CL), followed on Day 7 by an ovulatory dose of GnRH or pLH to synchronize ovulation. Insemination (e.g., artificial insemination) at detected estrus or following treatment with GnRH or pLH on Day 6 or 7 to synchronize ovulation (fixed-time artificial insemination [FTAI] on Day 7-7.5).

In another example, a prostaglandin such as Lutalyse is administered (e.g., about 5 mL Lutalyse® administered intramuscularly) followed (i.e., 48 h) by administration of Letrozole (i.e., 1-2 mg/Kg, intravenously) to synchronize individual cows of a herd with respect to the time of occurrence of estrus, ovulation, or both.

For the purposes of ovarian superovulation and embryo transfer, superstimulatory treatments may be initiated 36 to 48 hours after letrozole and GnRH/pLH treatment, as outlined in paragraph 158 above.

In another example of superovulation, Letrozole is administered (i.e., 1-2 mg/Kg, IV, SID for 4 days or a slow-release device containing letrozole) at the beginning of follicular wave emergence in a cow, concurrent with a conventional superstimulatory treatment protocol that is also initiated at wave emergence.

Synchronization of ovulation in a mare is notoriously difficult, owing primarily to a prolonged and variable follicular phase (63). Various combinations of reproductive steroids (progestogens and estrogens), prostaglandin-F2α (PGF, native and analogues), human chorionic gonadotropin (hCG) and gonadotropin-releasing hormone (GnRH, native and analogues) have been used to control follicular development and the time of ovulation for basic and applied purposes during the spring transition, estrous cycle and postpartum period in mares [review in 63].

From an applied perspective, the most common objectives are to coordinate the expected time of ovulation with insemination and align ovulations in recipient mares with donor mares in an embryo transfer program. Regimens of progestogens (injectable, oral and intravaginal) and PGF used alone or in combination have limited control on follicular development and, therefore, are primarily used to inhibit or delay ovulation. The hormonal regimen used most often to control both follicular development and ovulation is a combination of progesterone plus estradiol (P&E). The regimen involves intramuscular administration of P&E for 10 d beginning at unknown or random stages of the estrous cycle, PGF on the last day of steroid treatment and hCG or GnRH when the largest follicle reaches >35 mm.

According to seminal studies done in the 1980's, this steroidal regimen without hCG treatment resulted in ovulation synchrony among mares ranging from 54% to 68% within a 2-d period and from 72% to 94% within a 4-d period [reviewed in [63]. With hCG treatment, ovulation was synchronous among 70% to 73% of mares within a 2-d period after hCG treatment. In the latter study [9], the time to ovulation ranged from 8 to 17 d after the last steroid treatment or 18 to 27 d after the first steroid treatment. With an average interval of 22 d from the first steroid treatment to ovulation, a large portion (about 45%) of the interval involves daily handling of animals and steroid hormones.

Although effective, daily steroidal treatment is time consuming and labor intensive. In addition, repeated intramuscular or subcutaneous treatments increase the risk of injection-site inflammation and, as a consequence, some mares will become intolerant to immediate and future injections.

In the present application, treatment with letrozole (1-2 mg/Kg, IV, SID for 4 days or a slow-release device containing letrozole) may be applied on random days of the estrous cycle to induce the formation of a persistent dominant follicle and delay wave emergence by preventing spontaneous ovulations (i.e., inhibiting the pre-ovulatory rise in estradiol and potentially delaying luteolysis). On Day 5 (Day 0=day of treatment), a luteolytic dose of PGF is given to induce regression of the corpus luteum (CL), followed on Day 7 by an ovulatory dose of GnRH or pLH to synchronize ovulation. Insemination (e.g., artificial insemination) at detected estrus or following treatment with GnRH or pLH on Day 6 or 7 to synchronize ovulation (fixed-time artificial insemination [FTAI] on Day 7-7.5).

Improved Fertility

Letrozole treatment, given in early metestrus (about Day 1 post-ovulation) or mid-diestrus (about Day 9 post-ovulation) resulted in a luteotrophic effect, documented by larger CL diameter and greater plasma progesterone profiles in treated animals. Treatment during the early luteal phase increases CL viability and progesterone production, which is important for ensuring rapid growth of a healthy embryo and successful establishment of pregnancy. In high-producing dairy cows, for example, low levels of progesterone account for low pregnancy rates and high embryonic loss rates. Letrozole, (1-2 mg/Kg, IV, SID for 4 days or a slow-release device containing letrozole), is given one day after artificial insemination to promote development of the CL, resulting in a larger CL diameter and higher circulating concentrations of progesterone.

Similarly, letrozole treatment may be given so that its effect encompasses the period of maternal recognition of pregnancy (i.e., the time of luteal response to pregnancy). In cattle, letrozole treatment is initiated on or before 15 days after artificial insemination (maternal recognition of pregnancy is between Days 15 and 17 post-ovulation in cattle). Treatment at this time will promote the establishment of pregnancy through two mechanisms. Firstly, letrozole exerts a luteotrophic effect to enhance CL functionality and survival. Secondly, letrozole will compromise the luteolytic mechanism by decreasing circulating estradiol concentration which mediates the luteolytic process by stimulating the expression of oxytocin receptors in the endometrium, which are necessary for prostaglandin production and release. Again, this is a common problem in high producing dairy cattle; low levels of progesterone result in insufficient trophoblast expansion to block prostaglandin production and release from the uterus.

For embryo transfer recipients—letrozole treatment is initiated prior to ovulatory follicular wave emergence to induce co-dominance, and double ovulation. Letrozole (250 μg/kg/day) is given from Day 1 (Day 0=wave emergence) until Day 7. PGF is administered on day 5 followed by GnRH/LH treatment 36 h later. As a result, recipient animals will have more than one corpus luteum and higher progesterone levels to ensure a successful attachment and development of the transferred embryo. An alternative protocol for embryo transfer recipients is letrozole treatment, in a slow-release preparation, initiated one day after ovulation for 5 days to promote development of the new CL, resulting in a larger CL diameter and higher circulating concentrations of progesterone.

Twinning

As shown herein, letrozole treatment given before dominant follicle selection, induces the development of co-dominance; i.e., 2 dominant follicles. The data suggest that letrozole may be used to produce double ovulations and twin pregnancies with much higher efficiency than other previously explored treatments (e.g., eCG or FSH). The advantage of letrozole treatment is that it appears to induce the development of only two dominant follicles, which overcome the adverse effects of gonadotropin treatments where multiple (3 to 10) ovulations and conceptions commonly occur. In this regard, a letrozole-impregnated slow-releasing device may be applied on the day of or the day after follicle wave emergence of either an anovulatory or ovulatory follicular wave. On Day 5 after wave emergence, the letrozole device is removed and a luteolytic dose of PGF given. Artificial insemination at detected estrus or following treatment with GnRH or pLH on Day 6 or 7 to synchronize ovulation (FTAI) would be expected to result in twin pregnancies.

Inducing multiple ovulation in mares is difficult and expensive. Letrazole treatment (as described in paragraph 171 above) may be used in mares, with or without other superstimulatory hormones (e.g., FSH or equine pituitary extract), to induce multiple ovulation in mares for the purposes of embryo production and embryo transfer.

Induction of Ovulation in Women and Non-Human Primates

Letrozole treatment during the expected time of ovulation can be used to trigger the physiologic cascade of events leading to ovulation. Women treated with Letrozole at 18 mm follicle diameter ovulated 24 hours earlier than controls. This opens the possibility that Letrozole may be used to induce ovulation in place of either hCG or GnRH should it be advantageous to avoid the use of glycoprotein preparations.

Inhibition of Ovulation in Cattle and Other Ungulates

Letrozole treatment during the expected time of ovulation (during the late follicular phase of the estrous cycle) can be used to prevent the increase on estradiol concentration and therefore the LH surge that triggers ovulation. Treatment with letrozole during the pre-ovulatory wave in cattle delayed ovulation for 24 hr.

Ovarian Superstimulation

The addition of letrozole in superovulation protocols can reduce the mass/volume/dose of gonadotropins required to achieve a good ovarian response to the exogenous gonadotrophins or other ovarian stimulation protocols that may be used to increase the number and or quality of oocytes to be ovulated or removed via ovarian follicular aspiration. In addition, reducing the amount/volume/mass of gonadotropins required to generate an adequate ovarian response is expected to reduce the risk of ovarian hyperstimulation syndrome in women and other mammals where OHSS may be problematic.

The addition of letrozole in superovulation protocols can reduce the total dose of gonadotropins required to achieve the desired ovarian response to the exogenous gonadotrophins or other ovarian stimulation protocols that may be used to increase the number of ovulations or the number of oocytes collected via ovarian follicular aspiration. In addition, reducing the amount/volume/mass of gonadotropins required to generate an adequate ovarian response is expected to reduce the risk of ovarian hyperstimulation syndrome in women and other mammals where OHSS may be problematic.

Increase Fertility after Ovarian Superstimulation Treatment

Letrozole treatment during superovulation protocols can help to reduce the increased concentration of estradiol that is normally observed in superstimulated individuals, therefore favoring sperm transport and uterine maturation for future implantation as well as oocyte competence.

Letrozole treatment during superovulation protocols can help to reduce the increased concentration of estradiol associated with ovarian superstimulation, thereby enhancing sperm transport and uterine maturation for future implantation as well as oocyte competence.

REFERENCES

1. Bo, G. A., et al., *Exogenous control of follicular wave emergence in cattle. Theriogenology,* 1995. 43(1): p. 31-40.
2. Bo, G. A., et al., *Ovarian follicular wave emergence after treatment with progestogen and estradiol in cattle.* Anim Reprod Sci, 1995. 39(3): p. 193-204.

3. Bo, G. A., et al., *Local versus systemic effects of exogenous estradiol-17[beta] on ovarian follicular dynamics in heifers with progestogen implants*. Anim Reprod Sci, 2000. 59(3-4): p. 141-157.

4. Ginther, O. J., et al., *Selection of the dominant follicle in cattle: Role of estradiol*. Biol Reprod, 2000. 63(2): p. 383-389.

5. Rawlings, N. C., I. A. Jeffcoate, and D. L. Rieger, *The influence of estradiol-17[beta] and progesterone on peripheral serum concentrations of luteinizing hormone and follicle stimulating hormone in the ovariectomized ewe*. Theriogenology, 1984. 22(5): p. 473-488.

6. Price, C. A. and R. Webb, *Steroid control of gonadotropin secretion and ovarian function in heifers [published erratum appears in Endocrinology 1989 February; 124(2): 604]*. Endocrinology, 1988. 122(5): p. 2222-2231.

7. Ireland, J. J. and J. F. Roche, *Effect of progesterone on basal LH and episodic LH and FSH secretion in heifers*. J Reprod Fertil, 1982. 64(2): p. 295-302.

8. Adams, G. P., R. L. Matteri, and O. J. Ginther, *Effect of progesterone on ovarian follicles, emergence of follicular waves and circulating follicle-stimulating hormone in heifers*. J Reprod Fertil, 1992. 96(2): p. 627-640.

9. Savio, J. D., et al., *Effects of induction of low plasma progesterone concentrations with a progesterone-releasing intravaginal device on follicular turnover and fertility in cattle*. J Reprod Fertil, 1993. 98(1): p. 77-84.

10. Savio, J. D., et al., *Regulation of dominant follicle turnover during the oestrous cycle in cows*. J Reprod Fertil, 1993. 97(1): p. 197-203.

11. Stock, A. E. and J. E. Fortune, *Ovarian follicular dominance in cattle: relationship between prolonged growth of the ovulatory follicle and endocrine parameters*. Endocrinology, 1993. 132(3): p. 1108-1114.

12. Sanchez, T., et al., *Dosage of the synthetic progestin, norgestomet, influences luteinizing hormone pulse frequency and endogenous secretion of 17 beta-estradiol in heifers*. Biol Reprod, 1995. 52(2): p. 464-469.

13. Adams, G. P., *Control of ovarian follicular wave dynamics in cattle: Implications for synchronization & superstimulation*. Theriogenology, 1994. 41(1): p. 19-24.

14. Bridges, P. J., et al., *Follicular growth, estrus and pregnancy after fixed-time insemination in beef cows treated with intravaginal progesterone inserts and estradiol benzoate*. Theriogenology, 1999. 52(4): p. 573-583.

15. Martinez, M. F., et al., *Induction of follicular wave emergence for estrus synchronization and artificial insemination in heifers*. Theriogenology, 2000. 54(5): p. 757-769.

16. Colazo, M. G., et al., *Fertility following fixed-time AI in CIDR-treated beef heifers given GnRH or estradiol cypionate and fed diets supplemented with flax seed or sunflower seed*. Theriogenology, 2004. 61(6): p. 1115-1124.

17. Mapletoft, R. J., et al., *The use of controlled internal drug release devices for the regulation of bovine reproduction*. J Anim Sci, 2003. 81(14_suppl_2): p. E28-36.

18. Umberger, E. J., *Products marketed to promote growth in food-producing animals: Steroid and hormone products*. Toxicology, 1975. 3(1): p. 3-21.

19. Fritsche, S, and H. Steinhart, *Occurrence of hormonally active compounds in food: a review*. Eur Food Res Technol, 1999. 209(3): p. 153-179.

20. Daxenberger, A., D. Ibarreta, and H. H. D. Meyer, *Possible health impact of animal oestrogens in food*. Hum Reprod Update, 2001. 7(3): p. 340-355.

21. Andersson, A. and N. Skakkebaek, *Exposure to exogenous estrogens in food: possible impact on human development and health*. Eur J Endocrinol, 1999. 140(6): p. 477-485.

22. US Department of Agriculture. Foreign Agricultural Service 2003. *Historic overview and chronology of EU's hormone ban*. GAIN Report E23206. Available from http://www.fas.usda.gov/scriptsw/attacherep/gain_display_report.asp?Rep_ID=145986773.

23. Official Journal of the European Union, *L* 262, 14 Oct. 2003. *Directive 2003/74/EC of the European Parliament and of the Council on 22 Sep. 2003 amending Council Directive 96/22/EC concerning the prohibition on the use in stockfarming of certain substances having a hormonal or thyristatic action and of beta-agonist*. pp. 17-21. Brussels, Belgium, 2003.

24. Lane, E. A., E. J. Austin, and M. A. Crowe, *Oestrous synchronisation in cattle—Current options following the EU regulations restricting use of oestrogenic compounds in food-producing animals: A review*. Anim Reprod Sci, 2008. 109(1-4): p. 1-16.

25. Cohen, M. H., et al., *Approval summary: Letrozole in the treatment of postmenopausal women with advanced breast cancer*. Clin Cancer Res, 2002. 8(3): p. 665-669.

26. Health Canada. *Drugs and Health Products. Veterinary Products. Questions and answer: Hormonal growth promoters*. Accessed 25 *Jan.*, 2009. Available from http://www.hc-sc.gc.ca/dhp-mps/vet/faq/growth_hormones_promoters_croissance_hormonaux_stimulateurs-eng.php.

27. Gibbs, J. N., *Is veterinary compounding illegal under federal law?* IJPC, 2004. 8(6): p. 449-451.

28. US Food and Drug Administration, 2003. *Compliance Policy Guides Manual, Sec. 608.400. Compounding of drugs for use in animals*. Department of Health and Human Services. Available from http://www.fda.gov/ora/compliance_ref/cpg/cpgvet/cpg608-400compounding.pdf 29. Requena, A., et al., *Use of letrozole in assisted reproduction: A systematic review and meta-analysis*. Hum Reprod Update, 2008. 14(6): p. 571-582.

30. Mitwally, M. F. and R. F. Casper, *Aromatase inhibition for ovarian stimulation: future avenues for infertility management*. Curr Opin Obstet Gynecol, 2002. 14(3): p. 255-263

31. Al-Fadhli, R., et al., *A randomized trial of superovulation with two different doses of letrozole*. Fertil Steril, 2006. 85(1): p. 161-164.

32. Mitwally, M. F., et al., *Letrozole step-up protocol: A successful superovulation protocol*. Fertil Steril, 2008. 89(4, Supplement 1): p. S23-S24.

33. Pierson, R. A. and O. J. Ginther, *Reliability of diagnostic ultrasonography for identification and measurement of follicles and detecting the corpus luteum in heifers*. Theriogenology, 1987. 28(6): p. 929-936.

34. Hafs, H. D., et al., *Control of the estrous cycle with prostaglandin F2{alpha} in cattle and horses*. J Anim Sci, 1974. 38(Supplement_1): p. 10-21.

35. Berfelt, D. R., K. C. Lightfoot, and G. P. Adams, *Ovarian synchronization following ultrasound-guided transvaginal follicle ablation in heifers*. Theriogenology, 1994. 42(6): p. 895-907.

36. Adams, P., et al., *Selection of a dominant follicle and suppression of follicular growth in heifers*. Anim Reprod Sci, 1993. 30(4): p. 259-271.

37. Knopf, L., et al., *Ovarian follicular dynamics in heifers: Test of two-wave hypothesis by ultrasonically monitoring individual follicles*. Domest Anim Endocrinol, 1989. 6(2): p. 111-119.

38. Ginther, O. J., et al., *Emergence and deviation of follicles during the development of follicular waves in cattle.* Theriogenology, 1997. 48(1): p. 75-87.
39. Kastelic, J. P., L. Knopf, and O. J. Ginther, *Effect of day of prostaglandin F2[alpha] treatment on selection and development of the ovulatory follicle in heifers.* Anim Reprod Sci, 1990. 23(3): p. 169-180.
40. Peter, A. T., et al., *Compilation of classical and contemporary terminology used to describe morphological aspects of ovarian dynamics in cattle.* Theriogenology, 2009. 71(9): p. 1343-1357.
41. Sioufi, A., et al., *Absolute bioavailability of letrozole in healthy postmenopausal women.* Biopharm Drug Dispos, 1997. 18(9): p. 779-789.
42. Bergfelt, D. R., et al., *Surges of FSH during the follicular and early luteal phases of the estrous cycle in heifers.* Theriogenology, 1997. 48(5): p. 757-768.
43. Evans, A. C. O., G. P. Adams, and N. C. Rawlings, *Endocrine and ovarian follicular changes leading up to the first ovulation in prepubertal heifers.* J Reprod Fertil, 1994. 100(1): p. 187-194.
44. Valentini, F., et al., *An electrochemical ELISA procedure for the screening of 17-estradiol in urban waste waters.* Analyst, 2002. 127: p. 1333-1337.
45. Hecker, M., et al., *Effects of atrazine on CYP19 gene expression and aromatase activity in testes and on plasma sex steroid concentrations of male african clawed frogs (Xenopus laevis).* Toxicol Sci, 2005. 86(2): p. 273-280.
46. Mitwally, M. F. M. and R. F. Casper, *Single-dose administration of an aromatase inhibitor for ovarian stimulation.* Fertil Steril, 2005. 83(1): p. 229-231.
47. Mitwally, M. F. M. and R. F. Casper, *Aromatase inhibition reduces the dose of gonadotropin required for controlled ovarian hyperstimulation.* J Soc Gynecol Investig, 2004. 11(6): p. 406-415.
48. Mitwally, M. F. and R. F. Casper, *Use of aromatase inhibitor for induction of ovulation in patients with an inadequate response to clomiphene citrate.* Fertil Steril, 2001. 75: p. 305-309.
49. Mitwally, M. F. and R. F. Casper, *Aromatase Inhibition improves ovarian response to follicle-stimulating hormone in poor responders.* Fertil Steril, 2002. 77(4): p. 776-780.
50. Jee, B. C., et al., *Use of letrozole versus clomiphene citrate combined with gonadotropins in intrauterine insemination cycles: a pilot study.* Fertil Steril, 2006. 85(6): p. 1774-1777.
51. Cortinez, A., et al., *Hormonal profile and endometrial morphology in letrozole-controlled ovarian hyperstimulation in ovulatory infertile patients.* Fertil Steril, 2005. 83(1): p. 110-115.
52. Casper, R. F., *Letrozole: ovulation or superovulation?* Fertil Steril, 2003. 80(6): p. 1335-1337.
53. Bayar, U., et al., *Letrozole vs. clomiphene citrate in patients with ovulatory infertility.* Fertil Steril, 2006. 85(4): p. 1045-1048.
54. Sinha, S., et al., *Effect of CGS 20267 on ovarian aromatase and gonadotropin levels in the rat.* Breast Cancer Res Treat, 1998. 48(1): p. 45-51.
55. Baerwald, A., G. Adams, and R. Pierson, *Characterization of ovarian follicular wave dynamics in women.* Biol Reprod, 2003. 69(3): p. 1023-1031.
56. At-Taras, E. E., et al., *Reducing estrogen synthesis does not affect gonadotropin secretion in the developing boar.* Biol Reprod, 2006. 74(1): p. 58-66.
57. Miller, K. F., et al., *Ovarian effects of bovine follicular fluid treatment in sheep and cattle.* Biol Reprod, 1979. 21(3): p. 537-544.
58. Miller, K. F., J. A. Wesson, and O. J. Ginther, *Interaction of estradiol and a nonsteroidal follicular fluid substance in the regulation of gonadotropin secretion in the mare.* Biol Reprod, 1981. 24(2): p. 354-358.
59. Ginther, O. J., et al., *Mechanism of follicle deviation in monovular farm species.* Anim Reprod Sci, 2003. 78(3-4): p. 239-257.
60. Bleach, E. C. L., et al., *Plasma inhibin A in heifers: Relationship with follicle dynamics, gonadotropins, and steroids during the estrous cycle and after treatment with bovine follicular fluid.* Biol Reprod, 2001. 64(3): p. 743-752.
61. Sioufi, A., et al., *Comparative bioavailability of letrozole under fed and fasting conditions in 12 healthy subjects after a 2.5 mg single oral administration.* Biopharm Drug Dispos, 1997. 18(6): p. 489-497.
62. Mamali, P., et al. *The effect of albendazole administration on the concentration of ovarian steroids in the follicular fluid and the maturation of oocytes in the ewe. in 16th International Conference of Animal Reproduction.* 2008. Budapest, Hungary: Reprod Domest Anim.
63. Bergfelt D R, Meira C, Fleury J J, Fleury P D C, Dell'Aqua J A, Adams G P (2007) *Ovulation synchronization following commercial application of ultrasound-guided follicle ablation during the estrous cycle in mares.* Theriogenology 68:1183-1191.

Adams G P, Kot K, Smith C A, Ginther O J (1993) *Effect of the dominant follicle on regression of its subordinates in heifers.* Canadian Journal of Animal Science 73: 267-275.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

The invention claimed is:

1. A method of regulating ovarian follicle development and/or ovulation in a mammal, comprising:
 (a) administering an amount of an aromatase inhibitor effective to influence ovarian follicle wave emergence in said mammal;
 (b) administering a luteolytic dose of a prostaglandin or a suppressive dose of a gonadotropin-agonist or antagonist to prevent corpus luteum (CL) formation; and
 (c) administering an ovulatory dose of a compound selected from the group consisting of gonadotropin-releasing hormone (GnRH), a GnRH analogue, luteinizing hormone (LH), and an LH analogue
 wherein said prostaglandin is $PGF_{2\alpha}$, or a $PGF_{2\alpha}$ analogue, and wherein said $PGF_{2\alpha}$ or $PGF_{2\alpha}$ analogue is administered 3 to 7 days after initiating administration of said aromatase inhibitor,
 wherein said GnRH, GnRH analogue, LH, or LH analogue is administered within 48 hours after the last day of said aromatase inhibitor treatment.

2. The method of claim 1, wherein the aromatase inhibitor is letrozole or a letrozole analogue.

3. The method of claim 1, further comprising a step of inseminating said mammal.

4. The method of claim 1, wherein said mammal is a bovid.

5. The method of claim 1, wherein said aromatase inhibitor is administered using a slow-release device.

6. A method of synchronizing follicle wave emergence or ovulation in a plurality of mammals, comprising subjecting each of the plurality of mammals to the method of claim 1.

7. The method of claim 1, further comprising a step of inseminating said mammal following treatment with said GnRH, GnRH analogue, LH or LH analogue.

8. The method of claim 1, wherein said mammal is a human, a non-human primate, a cow, a hone, a pig, a dog, or a cat.

9. A method of regulating ovarian follicle development and/or ovulation in a mammal comprising:
   (a) administering an amount of an aromatase inhibitor effective to influence ovarian follicle wave emergence in said mammal;
   (b) administering a luteolytic dose of a prostaglandin or a suppressive dose of a gonadotropin-agonist or antagonist to prevent corpus luteum (CL) formation; and
   administering an ovulatory dose of a compound selected from the group consisting of gonadotropin-releasing hormone (GnRH), a GnRH analogue, luteinizing hormone (LH), and an LH analogue,
   wherein step (a) is carried out before step (b),
   wherein said GnRH, GnRH analogue, LH, or LH analogue is administered within 48 hours after the last day of said aromatase inhibitor treatment.

10. The method of claim 9, wherein the aromatase inhibitor is letrozole or a letrozole analog.

11. The method of claim 10, wherein administration of said letrozole or letrozole analogue is within 3 days following administration of said $PGF_{2\alpha}$, or $PGF_{2\alpha}$ analogue.

12. The method of claim 9, wherein said prostaglandin is $PGF_{2\alpha}$, or a $PGF_{2\alpha}$ analogue.

13. The method of claim 12, wherein said $PGF_{2\alpha}$, or $PGF_{2\alpha}$ analogue is administered 3 to 7 days after initiating administration of said aromatase inhibitor.

14. The method of claim 9, further comprising a step of inseminating said mammal.

15. The method of claim 9, wherein said mammal is a bovid.

16. The method of claim 9, wherein said aromatase inhibitor is administered using a slow-release device.

17. A method of synchronizing follicle wave emergence or ovulation in a plurality of mammals, comprising subjecting each of the plurality of mammals to the method of claim 9.

18. The method of claim 9, further comprising a step of inseminating said mammal following treatment with said GnRH, GnRH analogue, LH or LH analogue.

19. The method of claim 9, wherein said mammal is a human, a non-human primate, a cow, a hoe, a pig, a dogs, or a cat.

* * * * *